United States Patent [19]

Cheng

[11] 4,309,425

[45] Jan. 5, 1982

[54] MITICIDAL, INSECTICIDAL, OVICIDAL AND FUNGICIDAL N-(N',N'-DIARYLAMINOTHIO)SULFONAMIDES

[75] Inventor: Jiin-Duey Cheng, Wilmington, Del.

[73] Assignee: E. I. Du Pont de Nemours and Company, Wilmington, Del.

[21] Appl. No.: 134,883

[22] Filed: Apr. 11, 1980

Related U.S. Application Data

[63] Continuation-in-part of Ser. No. 69,752, Aug. 24, 1979, abandoned.

[51] Int. Cl.$^3$ .................. C07C 143/74; C07C 143/78
[52] U.S. Cl. ..................................... 424/244; 564/162; 564/166; 260/239.3 R; 564/176; 564/185; 260/326.5 S; 424/246; 424/267; 424/270; 424/248.5; 424/256; 424/272; 424/251; 424/274; 424/273 R; 424/309; 424/321; 424/273 P; 424/322; 424/324; 544/54; 544/97; 544/316; 546/216; 546/221; 548/186; 548/189; 548/229; 548/319; 560/12; 560/13; 560/16; 564/90; 564/91; 564/97; 564/99

[58] Field of Search ............... 424/246, 267, 244, 270, 424/248.5, 256, 272, 251, 274, 273 R, 309, 321, 273 P, 322, 324; 560/12, 13, 16; 564/79, 85, 87, 90, 91, 97, 99, 162, 166, 176, 185, 40; 260/326.5 S, 239.3 T; 544/54, 97, 316; 546/216, 221; 548/186, 189, 229, 319

[56] References Cited

U.S. PATENT DOCUMENTS

| | | | |
|---|---|---|---|
| 1,942,790 | 1/1934 | Zaucker et al. | 548/186 |
| 3,107,229 | 10/1963 | Malz et al. | 564/87 |
| 3,718,738 | 2/1973 | Fenyes | 424/32 H |
| 3,969,350 | 7/1976 | D'Amico et al. | 548/186 |
| 4,098,900 | 7/1978 | Dittrich et al. | 560/12 |
| 4,152,460 | 5/1979 | Dreikorn | 424/330 |
| 4,182,873 | 1/1980 | Janin | 548/189 |
| 4,246,283 | 1/1981 | Böger et al. | 564/91 |

FOREIGN PATENT DOCUMENTS

| | | |
|---|---|---|
| 156 | 6/1978 | European Pat. Off. |
| 2509416 | 3/1974 | Fed. Rep. of Germany |
| 2363602 | 6/1974 | Fed. Rep. of Germany |
| 1455207 | 10/1976 | United Kingdom |

OTHER PUBLICATIONS

Biba et al., Chem. Abst., 74, (1971), #141169b.

*Primary Examiner*—Arthur P. Demers

[57] ABSTRACT

Sulfonamides, such as N-[N-(2-chloro-5-(trifluoromethyl)phenyl]-N-[2,4-dinitro-6-(trifluoromethyl)phenyl]aminothio]-N,4-dimethylbenzenesulfonamide, are useful for control of arthropod pests of plants and animals and fungus disease of plants.

31 Claims, No Drawings

MITICIDAL, INSECTICIDAL, OVICIDAL AND FUNGICIDAL N-(N',N'-DIARYLAMINOTHIO)SULFONAMIDES

RELATED APPLICATIONS

This application is a continuation-in-part of my co-pending application U.S. Ser. No. 069,752, filed Aug. 24, 1979, now abandoned.

BACKGROUND OF THE INVENTION

This invention relates to insecticidal, miticidal, fungicidal and ovicidal sulfonamides, agricultural compositions containing them and methods of using them.

Belgian Pat. No. 826,376, discloses diphenylamine derivatives of the formula:

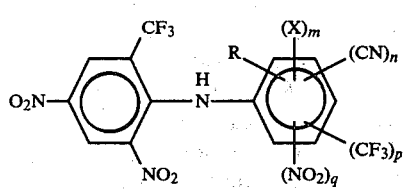

wherein
R is hydrogen, $C_{1-6}$ alkyl or alkoxy;
X is halogen;
m is zero or an integer from one to three;
n is zero or one;
p is zero, one or two;
q is zero, one or two; and
the sum of m, n, p and q is one, two or three.

Specifically disclosed in U.K. Pat. No. 1,455,207 is the compound 2,5'-bistrifluoromethyl-2'-chloro-4,6-dinitrodiphenylamine. The compounds are taught to have insecticidal, acaricidal and fungicidal properties.

European Patent Office Application 156 discloses 2-anilino-3,5-dinitrobenzotrifluoride derivatives of the formula:

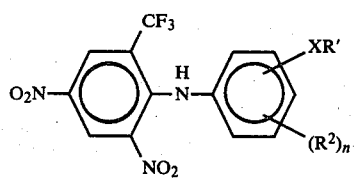

wherein
R' is alkyl substituted with halogen and/or haloalkoxy; phenyl optionally substituted with halogen, haloalkyl, haloalkoxy, haloalkylmercapto or haloalkylsulphonyl; or, when X=O, R' is unsubstituted alkyl;
$R^2$ is H, halogen, CN, $NO_2$ and/or alkyl optionally substituted with halogen and/or haloalkoxy; or XR' and $R^2$, when ortho to one another, may be linked so as to form (with the 2-adjacent C-atoms of the phenyl ring) an optionally substituted dioxanyl ring.

The application teaches that the disclosed compounds have insecticidal, acaricidal, nematocidal, insect growth retardant, fungicidal and bactericidal activity.

A substantial portion of the world's food supply is destroyed by pests and plant diseases. There is thus a continuing need for highly active insecticides, miticides, ovicides and fungicides.

SUMMARY OF THE INVENTION

According to this invention, compounds of the following formula have been discovered which are highly active miticides, insecticides, ovicides and fungicides and which cause minimal damage to desired crops.

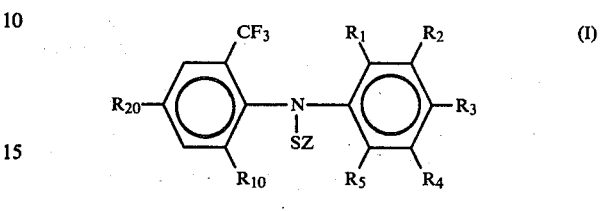

wherein
$R_1$, $R_3$ and $R_4$ are independently H, F, Cl, Br, $NO_2$, $CF_3$, $OCF_3$, $OCF_2CF_2H$ or $S(O)_kR_9$;
$R_2$ is H, F, Cl, Br, $NO_2$, $CF_3$ or $S(O)_kR_9$;
$R_5$ is H, Cl, F, Br or $NO_2$;
Z is $-NR_6SO_2R_{13}$, $$-NR_6\overset{\overset{O}{\|}}{C}R_{18} \quad \text{or} \quad -N\overset{\overset{O}{\|}}{C}\ ;$$
$$\phantom{xxxxxxxxxxxxxxxxxxxxxxxxxx}|$$
$$\phantom{xxxxxxxxxxxxxxxxxxxxxxxxxx}A$$

$R_6$ is $C_1$-$C_8$ alkyl, $C_3$-$C_5$ alkoxyalkyl, $C_2$-$C_4$ chloroalkyl,

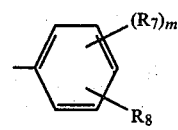

or $R_{14}CHCOR_{15}$;
$R_7$ is H, $C_1$-$C_4$ alkyl, $C_1$-$C_4$ alkoxy, Cl, Br or F;
$R_8$ is H, $C_1$-$C_{12}$ alkyl, $C_1$-$C_4$ alkoxy, Cl, Br, F, $CF_3$, $NO_2$, $R_{11}S(O)_k$ or $CO_2R_{12}$;
$R_9$ is $C_1$-$C_2$ alkyl or $C_1$-$C_2$ alkyl substituted with 2 to 4 atoms or Cl and/or F;
$R_{10}$ is H, $NO_2$ or $CF_3$;
$R_{11}$ is $C_1$-$C_2$ alkyl or $C_2$-$C_4$ dialkylamino,
$R_{12}$ is $C_1$-$C_4$ alkyl;
$R_{13}$ is

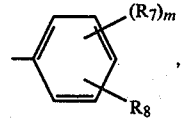

naphthyl, $NR_{16}R_{17}$, $CF_3$ or $C_1$-$C_{20}$ alkyl;
$R_{14}$ is H or $CH_3$;
$R_{15}$ is $C_1$-$C_4$ alkoxy or $N(R_{17})_2$;
$R_{16}$ is $C_1$-$C_3$ alkyl, $OCH_3$ or

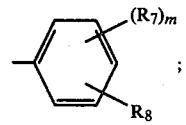

$R_{17}$ is $C_1$-$C_3$ alkyl;

$R_{18}$ is H, $C_1-C_8$ alkyl,

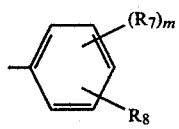

or $NR_{16}R_{17}$;

A is $-(CH_2)_3-$, $-(CH_2)_4-$, $-(CH_2)_5-$, $-X(CH_2)_2-$, or $-X(CH_2)_3-$, where X is O, S or $NR_{19}$ and where X is bonded to the carbonyl carbon of Z;

where X is O, S or $NR_{19}$ and where X is bonded to the carbonyl carbon of Z;

$R_{19}$ is $C_1-C_4$ alkyl, or phenyl optionally substituted with 1 or 2 groups selected from F, Cl, Br, $CH_3$ or $OCH_3$;

$R_{20}$ is $NO_2$ or $CF_3$;

k is 0, 1 or 2; and m is 1 or 2;

provided that (1) at least two of $R_1$, $R_2$, $R_3$, $R_4$ and $R_5$ are hydrogen;

(2) no more than two of the substituents $R_1$, $R_2$, $R_3$ and $R_4$ are simultaneously $NO_2$ or $CF_3$;

(3) when two $NO_2$ or two $S(O)_kR_9$ groups are present, they are not ortho to one another;

(4) only one of $R_6$ and $R_{13}$ or one of $R_6$ and $R_{16}$ or one of $R_6$ and $R_{18}$ is

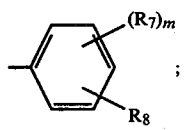

(5) when $R_{11}$ is dialkylamino, then k is 2; and (6) $R_{10}$ and $R_{20}$ are not simultaneously $CF_3$; and further provided that when $R_{10}$ is $NO_2$, then (a) $R_1$ is H, F or Cl when $R_3$ is other than H, F or Cl;

(b) when $R_1=R_3=R_5$, then $R_1$, $R_3$ and $R_5$ are either H or F; and (c) $R_5$ is either H or F.

Preferred Compounds

Preferred for reasons of lower cost, lower phytotoxicity and/or greater miticidal, insecticidal, ovicidal and/or fungicidal activity are those compounds of Formula I where independently:

$R_1$ is F, Cl, Br, $CF_3$, $OCF_3$, $OCF_2CF_2H$ or $S(O)_kCF_3$;

$R_2$ is H, F, Cl or Br;

$R_3$ is H, F, Cl, Br or $S(O)_kCF_3$;

$R_4$ is F, Cl, Br, $CF_3$, $OCF_3$, $OCF_2CF_2H$ or $S(O)_kCF_3$;

$R_6$ is $C_1-C_4$ alkyl;

$R_7$ is H, $C_1-C_3$ alkyl, $C_1-C_3$ alkoxy or Cl;

$R_8$ is H, $C_1-C_3$ alkyl or Cl;

$R_{10}$ is $NO_2$; and $R_{13}$ is

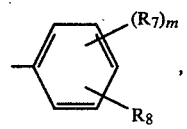

naphthyl, $NR_{16}R_{17}$ or $C_1-C_3$ alkyl, where $R_{16}$ and $R_{17}$ are independently $C_1-C_2$ alkyl.

More preferred for the same reasons are compounds of Formula I where independently:

$R_1$ and $R_4$ are independently Cl, $CF_3$, $OCF_3$, $OCF_2CF_2H$ or $S(O)_kCF_3$;

$R_3$ is H or $S(O)_kCF_3$;

$R_2$ and $R_5$ are H; and $R_{13}$ is

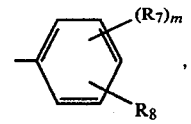

2-naphthyl, $N(CH_3)_2$ or $CH_3$.

Specifically preferred for excellent activity, lower phytotoxicity and lower cost are the compounds:

N-[N-[2-chloro-5-(trifluoromethyl)phenyl]-N-[2,4-dinitro-6-(trifluoromethyl)phenyl]aminothio]-N-4-dimethylbenzenesulfonamide;

N-butyl-N-[N-[2-chloro-5-(trifluoromethyl)phenyl]-N-[2,4-dinitro-6-(trifluoromethyl)phenyl]aminothio]-2-methylbenzenesulfonamide;

N-[N-[2-chloro-5-(trifluoromethyl)phenyl]-N-[2,4-dinitro-6-(trifluoromethyl)phenyl]aminothio]-4-methyl-N-(1-methylethyl)benzenesulfonamide;

N-butyl-N-[N-[2-chloro-5-(trifluoromethyl)phenyl]-N-[2,4-dinitro-6-(trifluoromethyl)phenyl]aminothio]-4-methylbenzenesulfonamide;

N-butyl-N-[N-[2-chloro-5-(trifluoromethyl)phenyl]-N-[2,4-dinitro-6-(trifluoromethyl)phenyl]aminothio]-benzenesulfonamide;

N-[N-[2-chloro-5-(trifluoromethyl)phenyl]-N-[2,4-dinitro-6-(trifluoromethyl)phenyl]aminothio]-N-(4-methylphenylsulfonyl)glycine methyl ester;

N-[N-[2,4-dinitro-6-trifluoromethyl)phenyl]-N-(2,4,6-trifluorophenyl)aminothio]-N,4-dimethylbenzenesulfonamide;

N-[2-chloro-5-(trifluoromethyl)phenyl]-N-[2,4-dinitro-6-(trifluoromethyl)phenyl]-2-oxo-1-pyrrolidinesulfenamide;

N-[N-[2-chloro-5-(trifluoromethyl)phenyl]-N-[2,4-dinitro-6-(trifluoromethyl)phenyl]aminothio]-N-methyl-2-naphthalenesulfonamide;

N-[N-[2-chloro-5-(trifluoromethyl)phenyl]-N-[2,4-dinitro-6-(trifluoromethyl)phenyl]aminothio]-N-butyl-N',N'-dimethylsulfamide;

N-butyl-N-[N-[2-chloro-5-(trifluoromethyl)phenyl]-N-[2,4-dinitro-6-(trifluoromethyl)phenyl]aminothio]-methanesulfonamide.

N-[N-[2-chloro-5-(trifluoromethyl)phenyl]-N-[2,4-dinitro-6-(trifluoromethyl)phenyl]aminothio]-N-(1,1-dimethylethyl)-4-methylbenzenesulfonamide; and N-[N-[2-chloro-5-(trifluoromethyl)phenyl]-N-[2,4-dinitro-6-trifluoromethylphenyl]aminothio]-N-(2-methoxyethyl)-4-methylbenzenesulfonamide.

Synthesis

The compounds of this invention, represented by Formula I, can be prepared by the reaction of an anion of the diphenylamine of Formula II with an equivalent or excess of the sulfenyl chloride, ClSZ, in a suitable solvent as illustrated by the following equation:

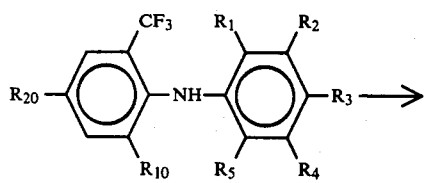

II

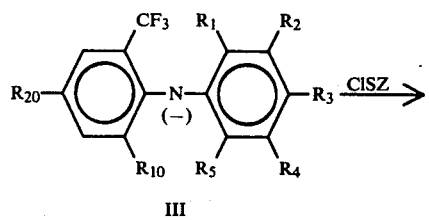

III

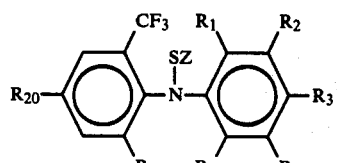

I

Aprotic solvents such as tetrahydrofuran (THF), dioxane, methylene chloride, chloroform and toluene are suitable for this reaction. The reaction temperature can be within the range of about −20° C. to 80° C., preferably about −10° C. to 30° C.

The anions of Formula III can be generated by treating compounds of Formula II with an equivalent amount or slight excess of a metal hydride such as sodium hydride or an alkali hydroxide such as potassium hydroxide in a suitable solvent at about −5° C. to 40° C.

Compounds of Formula I can also be prepared by the reaction of diphenylamines of Formula II with a sulfenyl chloride in the presence of an organic tertiary amine acid acceptor such as triethylamine, pyridine and the dialkylanilines, or an inorganic base such as potassium carbonate.

Diphenylamines of Formula II can be obtained by the procedures taught in Belgian Pat. No. 826,376 and European Patent Application 156, the disclosures of which are herein incorporated by reference. The N-chlorothiosulfonamides of the formula ClSZ can also be prepared by a suitable modification, obvious to one skilled in the art, of the procedure taught in British Pat. No. 1,403,170, herein incorporated by reference.

The following examples further illustrate the preparation of compounds of Formula I.

EXAMPLE 1

N-[N-[2-Chloro-5-(trifluoromethyl)phenyl]-N-[2,4-dinitro-6-(trifluoromethyl)phenyl]aminothio]-N,4-dimethylbenzenesulfonamide To a suspension of 0.25 g sodium hydride in 20 ml anhydrous THF was added 3.2 g of 2-[2′-chloro-5′-(trifluoromethyl)anilino]-3,5-dinitrobenzotrifluoride, in portions, at 10° to 20° C. After stirring for 30 minutes, a solution of 2 g of N-chlorothio-N-methyl-p-toluenesulfonamide in 20 ml dry THF was added rapidly at a temperature below −20° C. The mixture was stirred in an ice bath for 30 minutes, then quenched by careful addition of ether and water. The organic phase was washed once with water, dried over anhydrous magnesium sulfate and filtered. The filtrate was concentrated in vacuo. The resultant oil was crystallized from a mixture of hexane and chlorobutane to give 3.2 g of N-[N-[2-chloro-5-(trifluoromethyl)-phenyl]-N-[2,4-dinitro-6-(trifluoromethyl)phenyl]-aminothio]-N,4-dimethylbenzenesulfonamide, mp 142.5°–144° C.

Calculated for $C_{22}H_{15}ClF_6N_4O_6S_2$: C: 40.97, H: 2.34, N: 8.69, S: 9.94, Cl: 5.50 Found: C: 41.20, H: 2.42, N: 8.98, S: 10.00, Cl: 5.68.

The procedure described in Example 1 may be used to prepare the compounds in Tables 1 through 4.

TABLE 1

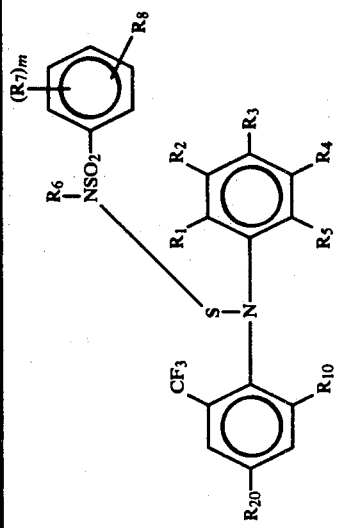

| R₁ | R₂ | R₃ | R₄ | R₅ | R₆ | R₇ | R₈ | R₁₀ | R₂₀ | m.p.(°C.) |
|---|---|---|---|---|---|---|---|---|---|---|
| Cl | H | H | CF₃ | H | n-Bu | 2-CH₃ | H | NO₂ | NO₂ | 49–66 (glass) |
| Cl | H | H | CF₃ | H | i-Pr | 4-CH₃ | H | NO₂ | NO₂ | (glass) |
| Cl | H | H | CF₃ | H | CH₃ | 4-Cl | H | NO₂ | NO₂ | 144–146 |
| Cl | H | H | CF₃ | H | CH₃OCH₂CH₂— | H | 4-CH₃ | NO₂ | NO₂ | 132.5–134.5 |
| Cl | H | H | CF₃ | H | CH₃ | H | H | NO₂ | NO₂ | 187–189 (dec.) |
| Cl | H | H | CF₃ | H | CH₃ | 2,5-(CH₃)₂ | H | NO₂ | NO₂ | |
| Cl | H | H | CF₃ | H | CH₃ | 2,4-Cl₂ | 6-CH₃O | NO₂ | NO₂ | 146.5–149 |
| Cl | H | H | CF₃ | H | CH₃ | 4-Cl | 3-CF₃ | NO₂ | NO₂ | 145–151 |
| Cl | H | H | CF₃ | H | CH₃ | 4-CH₃O | H | NO₂ | NO₂ | |
| Cl | H | H | CF₃ | H | ClCH₂CH₂— | H | 4-CH₃ | NO₂ | NO₂ | 195–196 |
| Cl | H | H | CF₃ | H | CH₃ | 2-Cl | 5-Cl | NO₂ | NO₂ | |
| Cl | H | H | CF₃ | H | CH₃ | 3-Cl | 4-Cl | NO₂ | NO₂ | 176–178.5(dec.) |
| Cl | H | H | CF₃ | H | CH₃ | H | 2-NO₂ | NO₂ | NO₂ | |
| Cl | H | H | CF₃ | H | CH₃ | H | 4-NO₂ | NO₂ | NO₂ | 80–96 (dec.) |
| Cl | H | H | CF₃ | H | CH₃ | H | 4-F | NO₂ | NO₂ | |
| Cl | H | H | CF₃ | Cl | CH₃ | H | 4-Br | NO₂ | NO₂ | |
| Cl | CF₃ | Cl | H | H | CH₃ | H | 4-t-Bu | NO₂ | NO₂ | |
| Cl | H | Cl | H | Br | CH₃ | 5-Br | 4-n-BuO | NO₂ | NO₂ | |
| Cl | Br | H | Br | H | i-PrOCH₂CH₂— | 3-F | 2-CH₃O | H | NO₂ | |
| Cl | H | H | CF₃ | H | Cl(CH₂)₄— | 4-CH₃ | H | H | NO₂ | |
| H | H | H | CF₃ | H | CH₃ | 4-CH₃ | H | NO₂ | NO₂ | 135–136.5 (dec.) |
| H | H | Cl | H | H | CH₃ | 4-CH₃ | H | NO₂ | NO₂ | 67–72 (dec.) |
| Cl | H | H | CF₃ | F | n-Bu | 4-CH₃ | 2-NO₂ | NO₂ | NO₂ | 116.5–118 |
| Cl | H | H | H | NO₂ | t-Bu | 4-CH₃ | 2-NO₂ | NO₂ | NO₂ | 166–167.5 |
| F | H | F | NO₂ | H | n-C₈H₁₇ | H | 2-NO₂ | NO₂ | NO₂ | |
| H | Cl | H | H | H | CH₃ | 4-CH₃ | H | H | NO₂ | |
| Cl | F | Cl | H | F | CH₃ | 4-CH₃ | H | NO₂ | NO₂ | |
| F | Cl | H | H | F | CH₃ | 4-CH₃ | H | NO₂ | NO₂ | |
| H | H | H | H | H | CH₃ | 4-CH₃ | H | NO₂ | NO₂ | |
| H | CHF₂CF₂S | H | H | H | CH₃ | 4-CH₃ | H | NO₂ | NO₂ | |

TABLE 1-continued

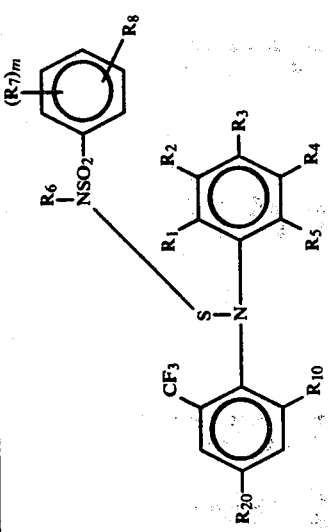

| R1 | R2 | R3 | R4 | R5 | R6 | R7 | R8 | R10 | R20 | m.p.(°C.) |
|---|---|---|---|---|---|---|---|---|---|---|
| H | CHF2CF2SO2 | H | H | H | CH3 | 4-CH3 | H | NO2 | NO2 | |
| H | CH3 | H | H | H | CH3 | 4-CH3 | H | NO2 | NO2 | |
| NO2 | H | Cl | CF3 | H | CH3OCH2CH2— | 4-CH3 | H | H | NO2 | 78–80 |
| HCF2CF2O | H | H | Cl | H | —CH2CO2CH3 | 4-CH3 | H | NO2 | NO2 | |
| CF3S | H | H | H | H | CH3 | 4-CH3 | H | NO2 | NO2 | |
| CH3SO2 | H | H | H | H | CH3 | 4-CH3 | H | NO2 | NO2 | |
| C2H5SO2 | H | H | H | H | CH3 | 4-CH3 | H | NO2 | NO2 | |
| CF3 | H | H | H | H | CH3 | 4-CH3 | H | NO2 | NO2 | |
| CHCl2CCl2S | H | H | H | H | CH3 | 4-CH3 | H | NO2 | NO2 | |
| Cl | H | H | Cl | H | CH3 | 4-CH3 | 4-t-Bu | NO2 | NO2 | 90–93 |
| Cl | H | H | CF3 | H | n-Bu | 4-CH3 | H | NO2 | NO2 | |
| Cl | CHCl2CCl2S | H | CF2HCF2O | H | CH3 | 4-CH3 | H | NO2 | NO2 | |
| Cl | H | NO2 | CH3S | H | CH3 | H | H | NO2 | NO2 | |
| Cl | NO2 | CF3 | CF3S | H | CH3 | 4-CH3 | H | NO2 | NO2 | |
| Cl | H | CF3S | CHCl2CCl2S | H | CH3 | 4-CH3 | H | NO2 | NO2 | |
| Cl | H | CF2HCF2O | CF3SO2 | H | t-Bu | 4-CH3 | H | NO2 | NO2 | 65–67 |
| Cl | H | CH3S | C2H5S | H | CH3 | H | H | NO2 | NO2 | |
| Cl | H | C2H5SO2 | H | H | t-Bu | 4-CH3 | H | NO2 | NO2 | |
| H | H | CF2HCF2O | CF3 | H | t-Bu | H | H | NO2 | NO2 | |
| Cl | H | H | CF3 | H | CH3 | 4-CH3 | n-C12H25 | NO2 | NO2 | |
| H | H | H | F | H | CH3 | 4-CH3 | H | NO2 | NO2 | |
| H | H | H | H | H | CH3 | 4-CH3 | H | NO2 | NO2 | |
| Cl | H | H | H | H | CH3 | 4-CH3 | H | NO2 | NO2 | |
| Cl | H | H | H | H | CH3 | 4-CH3 | H | NO2 | NO2 | |
| H | H | H | H | H | CH3 | 4-CH3 | H | NO2 | NO2 | |
| H | H | H | H | H | CH3 | 4-CH3 | H | NO2 | NO2 | |
| H | CF3S | H | CF3 | H | CH3 | 4-CH3 | H | NO2 | NO2 | |
| Cl | C2H5S | H | CF3 | H | CH3 | 4-CH3 | H | NO2 | NO2 | |
| Cl | Cl | CF3O | CF3 | H | CH3OCH2CH2— | 4-Cl | H | NO2 | NO2 | 134–137 |
| Cl | H | H | CF3 | H | n-Bu | 4-CH3 | H | NO2 | NO2 | 135–137 |
| Cl | H | H | CF3 | H | n-Bu | H | H | NO2 | NO2 | 114–118 |

TABLE 1-continued

| R1 | R2 | R3 | R4 | R5 | R6 | R7 | R8 | R10 | R20 | m.p.(°C.) |
|---|---|---|---|---|---|---|---|---|---|---|
| Cl | H | H | CF3 | H | Et | 4-t-Bu | H | NO2 | NO2 | |
| Cl | H | H | CF3 | H | Et | 4-n-BuO | H | NO2 | NO2 | |
| Cl | H | H | CF3 | H | CH3 | 4-i-Pr | H | NO2 | NO2 | |
| Cl | H | H | CF3 | H | CH3 | H | 4-CH3SO2 | NO2 | NO2 | |
| Cl | H | H | CF3 | H | CH3 | H | 4-EtSO2 | NO2 | NO2 | |
| Cl | H | H | CF3 | H | CH3 | H | 2-Me2NSO2 | NO2 | NO2 | |
| Cl | H | H | CF3 | H | CH3 | H | 2-Et2NSO2 | NO2 | NO2 | |
| Cl | H | H | H | H | CH3 | H | 3-CO2CH3 | NO2 | NO2 | |
| H | H | CHCl2CCl2S | CF3 | H | CH3 | H | 3-CO2Bu—n | NO2 | NO2 | |
| Cl | H | H | CF3 | H | sec-Bu | H | CH3 | NO2 | NO2 | glass |
| Cl | H | H | CF3 | H | t-Bu | 4-F | H | NO2 | NO2 | 134–136 (dec.) |
| Cl | H | H | CF3 | H | n-Bu | H | 4-F | NO2 | NO2 | 115–119° |
| Cl | H | H | CF3 | H | n-Bu | H | 4-Cl | NO2 | NO2 | 167–168.5 (dec.) |
| Cl | H | H | CF3 | H | t-Bu | 4-Cl | H | NO2 | NO2 | 154.5–155.5 (dec.) |
| Cl | H | H | CF3 | H | t-Bu | H | H | NO2 | NO2 | 95–97.5° |
| Cl | H | H | CF3 | H | n-Bu | H | 4-CH3 | NO2 | NO2 | 109–112° |
| Cl | H | H | CF3 | H | —CH3 | H | 3-CF3 | NO2 | NO2 | 134.5–136.5° |
| Cl | H | H | OCF3 | H | CH3 | H | 3-CF3 | NO2 | NO2 | mixture glass |
| | | | | | | | 4-CH3 | | | |
| OCF3 | H | H | Cl | H | CH3 | H | 4-CH3 | NO2 | NO2 | |
| Cl | H | H | CF3 | H | n-C8H17 | H | H | NO2 | NO2 | |
| Cl | H | H | CF3 | H | CH3 | H | H | CF3 | CF3 | |
| Cl | H | H | CF3 | H | CH3CHCO2CH2 | H | 4-CH3 | NO2 | NO2 | |
| | | | | | CH3 | | | | | |
| Cl | H | H | CF3 | H | —CH2CON | H | 4-CH3 | NO2 | NO2 | |
| | | | | | CH3 | | | | | |
| Cl | H | H | CF3 | H | —CH2CO2(CH2)3CH3 | H | H | NO2 | NO2 | |
| Cl | H | H | CF3 | H | —CH2CON(n-Pr)2 | H | H | NO2 | NO2 | |
| F | F | F | H | F | CH3 | H | H | NO2 | NO2 | |
| Br | H | H | CF3 | H | CH3 | H | H | NO2 | NO2 | |

TABLE 2

Structure: Diphenylamine with CF₃ and R₁₀ on one ring, R₁-R₅ on other ring; N-S-N(R₆)SO₂R₁₃ substituent; R₂₀ on first ring.

| R₁ | R₂ | R₃ | R₄ | R₅ | R₆ | R₁₃ | R₁₀ | R₂₀ | m.p.(°C.) |
|---|---|---|---|---|---|---|---|---|---|
| Cl | H | H | CF₃ | H | CH₃ | 2-naphthyl | NO₂ | NO₂ | 94–105 (dec.) glass |
| Cl | H | H | CF₃ | H | CH₃ | 1-naphthyl | NO₂ | NO₂ | |
| Cl | H | H | CF₃ | H | n-Bu | N(CH₃)₂ | NO₂ | NO₂ | 150–152 (dec.) |
| Cl | H | H | CF₃ | H | n-C₈H₁₇ | N(CH₃)₂ | NO₂ | NO₂ | |
| Cl | H | H | CF₃ | H | CH₃ | N(CH₃)₂ | NO₂ | NO₂ | |
| F | H | F | H | F | CH₃CHCO₂CH₃ | N(CH₃)₂ | NO₂ | NO₂ | |
| Cl | H | H | CF₃ | H | C₆H₅ | N(CH₃)₂ | NO₂ | NO₂ | |
| Cl | H | H | CF₃ | H | 3,5-Cl₂C₆H₃ | N(CH₃)₂ | NO₂ | NO₂ | |
| Cl | H | H | CF₃ | H | 4-ClC₆H₄ | N(CH₃)₂ | NO₂ | NO₂ | |
| Cl | H | H | CF₃ | H | 4-CH₃C₆H₄ | N(CH₃)₂ | NO₂ | NO₂ | |
| Cl | H | H | CF₃ | H | 4-FC₆H₄ | N(CH₃)₂ | NO₂ | NO₂ | |
| Cl | H | H | CF₃ | H | n-Bu | N(CH₃)(OCH₃) | NO₂ | NO₂ | |
| Cl | H | H | CF₃ | H | n-Bu | N(n-Pr)₂ | NO₂ | NO₂ | |
| F | H | F | H | F | n-Bu | CF₃ | NO₂ | NO₂ | |
| Cl | H | H | CF₃ | H | C₆H₅ | CH₃ | NO₂ | NO₂ | |
| Cl | H | H | CF₃ | H | 4-ClC₆H₄ | CH₃ | NO₂ | NO₂ | |
| Cl | H | H | CF₃ | H | 4-FC₆H₄ | CH₃ | NO₂ | NO₂ | |
| Cl | H | H | CF₃ | H | 4-CH₃C₆H₄ | CH₃ | NO₂ | NO₂ | |
| Cl | H | H | CF₃ | H | n-Bu | CH₃ | NO₂ | NO₂ | 163.5–166 (dec.) |
| Cl | H | H | CF₃ | H | CH₃ | CH₃ | NO₂ | NO₂ | |
| Cl | H | H | CF₃ | H | CH₃ | C₂₀H₄₁ | NO₂ | NO₂ | |
| Cl | H | H | CF₃ | H | t-Bu | CH₃ | NO₂ | NO₂ | |
| Cl | H | H | CF₃ | H | CH₃ | n-C₆H₁₃ | NO₂ | NO₂ | |
| Cl | H | H | CF₃ | H | CH₃ | C₆H₅NCH₃ | NO₂ | NO₂ | |
| Cl | H | H | CF₃ | H | n-Bu | 4-FC₆H₄NCH₃ | NO₂ | NO₂ | |
| Cl | H | H | CF₃ | H | CH₃ | C₆H₅N(n-Pr) | NO₂ | NO₂ | |
| Cl | H | H | CF₃ | H | CH₃ | CF₃ | NO₂ | NO₂ | |
| Cl | H | H | CF₃ | H | n-Bu | CF₃ | NO₂ | NO₂ | |
| Cl | H | H | CF₃ | H | n-Bu | N(CH₃)₂ | NO₂ | CF₃ | |
| Cl | H | H | CF₃ | H | CH₃ | N(CH₃)₂ | CF₃ | NO₂ | |
| Cl | H | H | CF₃ | H | CH₃ | 2-naphthyl | CF₃ | NO₂ | |
| Cl | H | H | CF₃ | H | CH₃ | CF₃ | CF₃ | NO₂ | |
| Cl | H | H | CF₃ | H | CH₃ | CH₃ | CF₃ | NO₂ | |
| Cl | H | H | CF₃ | H | CH₃ | C₆H₅NCH₃— | CF₃ | NO₂ | |

TABLE 3

Structure: Diphenylamine with CF₃ and R₁₀ on one ring, R₁-R₅ on other ring; N-S-N(C=O)-A (cyclic) substituent; R₂₀ on first ring.

| R₁ | R₂ | R₃ | R₄ | R₅ | A | R₁₀ | R₂₀ | m.p.(°C.) |
|---|---|---|---|---|---|---|---|---|
| Cl | H | H | CF₃ | H | —(CH₂)₃— | NO₂ | NO₂ | 114–118° |
| Cl | H | H | CF₃ | H | —(CH₂)₃— | NO₂ | NO₂ | |
| Cl | H | H | CF₃ | H | —O(CH₂)₂— | NO₂ | NO₂ | |
| Cl | H | H | CF₃ | H | —S(CH₂)₂— | NO₂ | NO₂ | |
| Cl | H | H | CF₃ | H | —N(CH₃)(CH₂)₂— | NO₂ | NO₂ | |

TABLE 3-continued $$\text{R}_{20}\text{-Ph(CF}_3\text{)(R}_{10}\text{)-N(SNC(=O)-A)-Ph(R}_1\text{)(R}_2\text{)(R}_3\text{)(R}_4\text{)(R}_5\text{)}$$

| $R_1$ | $R_2$ | $R_3$ | $R_4$ | $R_5$ | A | $R_{10}$ | $R_{20}$ | m.p.(°C.) |
|---|---|---|---|---|---|---|---|---|
| Cl | H | H | $CF_3$ | H | —N(n-Bu)(CH$_2$)$_2$— | $NO_2$ | $NO_2$ | |
| Cl | H | H | $CF_3$ | H | —N(3,5-Cl$_2$Ph)(CH$_2$)$_2$— | $NO_2$ | $NO_2$ | |
| Cl | H | H | $CF_3$ | H | —N(4-PPh)(CH$_2$)$_2$— | $NO_2$ | $NO_2$ | |
| Cl | H | H | $CF_3$ | H | —N(Ph)(CH$_2$)$_2$— | $NO_2$ | $NO_2$ | |
| Cl | H | H | $CF_3$ | H | —N(4-ClPh)(CH$_2$)$_2$— | $NO_2$ | $NO_2$ | |
| Cl | H | H | $CF_3$ | H | —N(4-CH$_3$Ph)(CH$_2$)$_2$— | $NO_2$ | $NO_2$ | |
| Cl | H | H | $CF_3$ | H | —N(4-BrPh)(CH$_2$)$_2$— | $NO_2$ | $NO_2$ | |
| Cl | H | H | $CF_3$ | H | —N(4-CH$_3$OPh)(CH$_2$)$_2$— | $NO_2$ | $NO_2$ | |
| Cl | H | H | $CF_3$ | H | —(CH$_2$)$_3$— | $NO_2$ | $CF_3$ | |
| Cl | H | H | $CF_3$ | H | —O(CH$_2$)$_2$— | $NO_2$ | $CF_3$ | |
| Cl | H | H | $CF_3$ | H | —N(CH$_3$)(CH$_2$)$_2$— | $CF_3$ | $NO_2$ | |
| Cl | H | H | $CF_3$ | H | —(CH$_2$)$_4$— | $NO_2$ | $NO_2$ | |
| Cl | H | H | $CF_3$ | H | —O(CH$_2$)$_3$— | $NO_2$ | $NO_2$ | |

TABLE 4

$$\text{R}_{20}\text{-Ph(CF}_3\text{)(R}_{10}\text{)-N(SNR}_6\text{CR}_{18}\text{=O)-Ph(R}_1\text{)(R}_2\text{)(R}_3\text{)(R}_4\text{)(R}_5\text{)}$$

| $R_1$ | $R_2$ | $R_3$ | $R_4$ | $R_5$ | $R_6$ | $R_{18}$ | $R_{10}$ | $R_{20}$ | m.p.(°C.) |
|---|---|---|---|---|---|---|---|---|---|
| Cl | H | H | $CF_3$ | H | $CH_3$ | $C_6H_5$ | $NO_2$ | $NO_2$ | |
| Cl | H | H | $CF_3$ | H | $CH_3$ | $CH_3$ | $NO_2$ | $NO_2$ | |
| Cl | H | H | $CF_3$ | H | $CH_3$ | n-$C_8H_{17}$ | $NO_2$ | $NO_2$ | |
| Cl | H | H | $CF_3$ | H | $CH_3$ | 4-$CH_3$Ph | $NO_2$ | $NO_2$ | |
| Cl | H | H | $CF_3$ | H | $CH_3$ | 4-ClPh | $NO_2$ | $NO_2$ | |
| Cl | H | H | $CF_3$ | H | $CH_3$ | 2,4-Cl$_2$Ph | $NO_2$ | $NO_2$ | |
| Cl | H | H | $CF_3$ | H | $CH_3$ | $C_6H_5$ | $CF_3$ | $NO_2$ | |
| Cl | H | H | $CF_3$ | H | $CH_3$ | $CH_3$ | $CF_3$ | $NO_2$ | |
| Cl | H | H | $CF_3$ | H | $CH_3$ | H | $NO_2$ | $NO_2$ | 102-108° |
| Cl | H | H | $CF_3$ | H | $CH_3$ | N(CH$_3$)$_2$ | $NO_2$ | $NO_2$ | |
| Cl | H | H | $CF_3$ | H | $CH_3$ | N(CH$_3$)(3,5-Cl$_2$Ph) | $NO_2$ | $NO_2$ | |
| Cl | H | H | $CF_3$ | H | $CH_3$ | N(OCH$_3$)(CH$_3$) | $NO_2$ | $NO_2$ | |
| Cl | H | H | $CF_3$ | H | $CH_3$ | —N(n-Pr)$_2$ | $NO_2$ | $NO_2$ | |

Formulation

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20-90 | 0-74 | 1-10 |
| Oil Suspensions, Emulsions, Solutions (including Emulsifiable Concentrates) | 5-50 | 40-95 | 0-15 |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation by tank mixing.

Typical solid diluents are described in Watkins et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York (1950). Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York (1964), list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147 ff. and "Perry's Chemical Engineer's Handbook", 4th Ed., McGraw-Hill, New York (1963), pp. 8–59 ff.

For further information regarding the art of formulation, see for example:

J. B. Buchanan, U.S. Pat. No. 3,576,834, Apr. 27, 1971, Col. 5, line 36 through Col. 7, line 70 and Ex. 1–4, 17, 106, 123–140.

R. R. Shaffer, U.S. Pat. No. 3,560,616, Feb. 2, 1971, Col. 3, line 48 through Col. 7, line 26, and Examples 3–9, 11–18.

E. Somers, "Formulation", Chapter 6 in Torgeson, "Fungicides", Vol. I, Academic Press, New York, 1967.

EXAMPLE 2

| Wettable Powder | |
|---|---|
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 65% |
| dodecylphenol polyethylene glycol ether | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE 3

| Wettable Powder | |
|---|---|
| N-butyl-N-[N-[2-chloro-5-(trifluoromethyl)-N-[2,4-dinitro-6-(trifluoromethyl)phenyl]aminothio]-2-methyl- | |

| -continued | |
|---|---|
| Wettable Powder | |
| benzenesulfonamide | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All of the compounds of this invention may be formulated in the same manner.

EXAMPLE 4

| High Strength Concentrate | |
|---|---|
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 98.5% |
| silica aerogel | 0.5% |
| synthetic amorphous fine silica | 1.0% |

The ingredients are blended and ground in a hammer mill to produce a high strength concentrate essentially all passing a U.S.S. No. 50 sieve (0.3 mm openings). This material may then be formulated in a variety of ways.

EXAMPLE 5

| Dust | |
|---|---|
| High strength concentrate, Example 3 | 25.4% |
| pyrophyllite, powdered | 74.6% |

The ingredients are thoroughly blended and packaged for use.

EXAMPLE 6

| Aqueous Suspension | |
|---|---|
| N-butyl-N-[N-[2-chloro-5-(trifluoromethyl)phenyl]-N-[2,4-dinitro-6-(trifluoromethyl)phenyl]aminothio]-2-methylbenzenesulfonamide | 50.0% |
| polyacrylic acid thickener | 0.3% |
| dodecylphenol polyethylene glycol ether | 0.5% |
| disodium phosphate | 1.0% |
| monosodium phosphate | 0.5% |
| polyvinyl alcohol | 1.0% |
| pentachlorophenol | 0.4% |
| water | 46.3% |

The ingredients are ground together in a sand mill to produce particles essentially all under five microns in size.

EXAMPLE 7

| Emulsifiable Concentrate | |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 20% |
| chlorobenzene | 74% |
| sodium monostearate and polyoxyethylene | |

| Emulsifiable Concentrate | |
|---|---|
| condensates thereof | 6% |

The ingredients are combined and stirred to produce a solution which can be emulsified in water for application.

Utility

The compounds of this invention may be used in several ways. First, they may be used to control arthropod pests of plant and animal. These include mites, insects and ticks.

As miticides, they may be used to protect plants from damage caused by these pests. More specifically, fruits, field crops, vegetables and ornamentals can be protected.

When mites come into contact with the compounds of this invention, either in the form of direct sprays or by walking over surfaces which have been treated, they are killed if they have been exposed to a sufficiently high dosage. While most plants are able to tolerate the presence of very small numbers of mites without adverse effect, the reproductive capacity of these pests is enormous. Generally, mite populations rapidly build up, easily out-stripping parasite and predator capabilities for control. Growers noting rapid mite build-up must take immediate action to prevent damage to economically important crops. Thus, there is a need for immediately reducing mite build-up and thereby preventing damage to important crops.

The method of this invention, namely, contacting mites with a miticidally effective concentration, is a most desirable method for control of these pests. This may be accomplished by applying an effective amount of a compound of this invention to the locus of infestation, to the area to be protected or to the pests themselves.

The quantity of compound needed for miticidal activity will vary depending on the specific situation; generally, a very small quantity is required. Among the variables that must be considered in deciding on the quantity of chemical to be used are the specific compound itself, the specific mite to be controlled, weather conditions, the type of crop, the stage of development of the crop, the volume of spray applied, population pressure, and the interval between applications. For plant protection, solutions or suspensions containing as little as 2.5 ppm of active ingredient in a spray solution may prove effective in a given set of circumstances. For field usage, however, in high-volume applications, aqueous spray preparations containing 5–2500 ppm of active ingredient are generally useful. Preferred are suspensions containing 20–500 ppm, and most preferred are those containing 80–320 ppm. On an area basis, in general, 0.03 to 5.5 kilograms of active ingredient per hectare are acceptable, preferably 0.03 to 3 kilograms, and most preferably, 0.06 to 2 kg. When applied in an orchard, spraying is continued until run-off is observed.

The compounds are especially suited for the protection of living plants such as fruit-bearing trees, nut-bearing trees, ornamental trees, forest trees, vegetable crops, horticultural crops (including ornamentals, small fruit and berries) and grain and seed crops. Apple trees, peach trees, cotton, citrus trees, beans and peanuts are particularly susceptible to mite damage and can be protected by application of the compounds of this invention. To assure control throughout the growing season (e.g., June through August in the Northern Hemisphere) multiple applications at desired intervals can be utilized.

Many species of mites are controlled by the compounds of this invention. The following is a list of representative susceptible mites along with the types of damage that they can cause: *Panonychus ulmi* (European red mite) and *Tetranychus urticae* (two-spotted mite) which are commonly called "orchard mites," and which attack a great many deciduous trees, such as apple, pear, cherry, plum and peach trees; *Tetranychus atlanticus* (Atlantic or strawberry mite), *T. cinnabarinus* (carmine spider mite) and *T. pacificus* (Pacific mite); which attack cotton and numerous other crop plants; *Panonychus citri* (citrus red mite) and others which attack citrus; *Phyllocoptruta oleivora* which causes citrus rust; *Byrobia praetiosa* (clover mite) which attacks clover, alfalfa and other crops; and *Eriophyes erinea* which attacks grasses and other plants.

EXAMPLE 8

Test units consisted of plant pots containing two red kidney bean plants in the two-leaf stage per pot. The plants were infested with two-spotted mites and sprayed to run-off with solutions of N-butyl-N-[N-[2-chloro-5-(trifluoromethyl)phenyl]-N-[2,4-dinitro-6-(trifluoromethyl)phenyl]aminothio]-2-methylbenzenesulfonamide. Dispersions were made by dissolving weighed quantities of the active ingredients in 10 ml of acetone and then diluting to volume with water containing 1:3000 of a surfactant, Duponol ® (a trade name of E. I. du Pont de Nemours and Co. for sodium alcohol sulfate). Mortality was evaluated two days after spraying.

| % Spray Concentration | % Mortality (2 days) |
|---|---|
| .001 | 100 |
| .0005 | 100 |
| .00025 | 100 |

EXAMPLE 9

Bean plants, infested with two-spotted mites, were sprayed to run-off with the indicated concentration of N-[N-[2-chloro-5-(trifluoromethyl)phenyl]-N-[2,4-dinitro-6-(trifluoromethyl)phenyl]aminothio]-4-methyl-N-(1-methylethyl)benzenesulfonamide in Duponol ®:water at 1:3000. Mortality after two days is set forth below.

| % Spray Concentration | % Mortality (2 days) |
|---|---|
| .001 | 100 |
| .0005 | 100 |
| .00025 | 100 |

EXAMPLE 10

Bean plants, infested with two-spotted mites, were sprayed to run-off with the indicated concentration of N-[N-[2-chloro-5-(trifluoromethyl)phenyl]-N-[2,4-dinitro-6-(trifluoromethyl)phenyl]aminothio]-N,4-dimethylbenzenesulfonamide in Duponol ®:water at 1:3000. Mortality after two days are as follows:

| % Spray Concentration | % Mortality (2 days) |
|---|---|
| .001 | 100 |
| .0005 | 100 |
| .00025 | 100 |

EXAMPLE 11

Test units consisted of plant pots containing two red kidney bean plants in the two-leaf stage per pot. The plants were infested with organo-phosphorous resistant two-spotted spider mites and sprayed to run-off with solutions of N-butyl-N-[N-[2-chloro-5-(trifluoromethyl)phenyl]-N-[2,4-dinitro-6-(trifluoromethyl)-phenyl]aminothio]-2-methylbenzenesulfonamide. Dispersions were made by dissolving weighed quantities of the active ingredient in 10 ml of acetone and then diluting to volume with water containing 1:3000 of a surfactant, Duponol®. Mite mortality was examined two days after spraying.

| % Spray Concentration | % Mortality (2 days) |
|---|---|
| .0020 | 100 |
| .0010 | 89 |
| .0005 | 90 |

EXAMPLE 12

Test units consisted of plant pots containing two red kidney bean plants in the two-leaf stage per pot. The plants were infested with organo-phosphorous resistant two-spotted spider mites and sprayed to run-off with solutions of N-[N-[2-chloro-5-(trfluoromethyl)phenyl]-N-[2,4-dinitro-6-(trifluoromethyl)phenyl]-aminothio]-4-methyl-N-(1-methylethyl)benzenesulfonamide. Dispersions were made by dissolving weighed quantities of the active ingredient in 10 ml acetone and then diluting to volume with water containing 1:3000 of a surfactant, Duponol®. Mite mortality was evaluated two days after spraying.

| % Spray Concentration | % Mortality (2 days) |
|---|---|
| .0020 | 99 |
| .0010 | 99 |
| .0005 | 83 |

EXAMPLE 13

Test units consisted of plant pots containing two red kidney bean plants in the two-leaf stage per pot. The plants were infested with organo-phosphorous resistant two-spotted spider mites and sprayed to run-off with solutions of N-[N-[2-chloro-5-(trifluoromethyl)phenyl]-N-[2,4-dinitro-6-(trifluoromethyl)phenyl]aminothio]-N,4-dimethylbenzenesulfonamide. Dispersions were made by dissolving weighed quantities of the active ingredient in 10 ml of acetone and then diluting to volume with water containing 1:3000 of a surfactant, Duponol®. Mite mortality was evaluated two days after spraying.

| % Spray Concentration | % Mortality (2 days) |
|---|---|
| .0020 | 100 |
| .0010 | 97 |
| .0005 | 93 |

The compounds of this invention are useful for the control of insects. Both the eggs and the motile forms are susceptible. The insects or insect eggs are controlled by applying the material in a convenient formulation to the locus of infestation, to the area to be protected, or to the pests themselves. For the control of insects in agricultural crops, the compound is generally applied to the foliage or other plant parts which are to be protected. Effective amounts to be applied depend on the species to be controlled, its life stage, its size and location and other variables. In general, 0.1 to 10 kg/ha may be required for insect control in agriculture with rates of 0.25 to 4 kg/ha usually being sufficient. Preferred rates in large scale operations are in the range of 0.3 to 2 kg/ha.

The insect species that may be controlled by ovicidal action of the compounds of this invention include, but are not limited to, *Spodoptera exigua* (beet armyworm), *Spodoptera frugiperda* (southern armyworm), *Phthorimaea operculella* (potato tuberworm), *Heliothis zea* (cotton bollworm) and *Heliothis viresceus* (tobacco budworm). These compounds are especially useful for controlling mosquito larvae. Motile stages of insects that may be controlled include, but are not limited to, *Anthonomus grandis* (cotton boll weevil), *Aphis fabae* (bean aphid), *Myzus persicae* (green peach aphid), *Epilachna varusestis* (Mexican bean beetle) *Melanoplus femurrubrum* (redlegged grasshopper), and *Camponotus pennsylvanicus* (black carpenter ant).

EXAMPLE 14

Eggs of the beet armyworm (*Spodoptera exigua*), laid on cellophane discs each containing 50–75 eggs, were placed in petri dishes and lightly sprayed with 1% concentrations of the indicated compounds in acetone solution. Three days later, percent control (% eggs failing to hatch) was determined.

| Compounds | % Control |
|---|---|
| N-butyl-N-[N-[2-chloro-5-(trifluoromethyl)phenyl]-N-[2,4-dinitro-6-(trifluoromethyl)phenyl]aminothio]-2-methylbenzenesulfonamide | 100 |
| N-[N-[2-chloro-5-(trifluoromethyl)phenyl]-N-[2,4-dinitro-6-(trifluoromethyl)phenyl]aminothio]-N,4-dimethyl-benzenesulfonamide | 100 |
| N-[2-chloro-5-(trifluoromethyl)phenyl]-N-[2,4-dinitro-6-(trifluoromethyl)phenyl]-2-oxo-1-pyrrolidinesulfenamide | 100 |
| N-[N-[2-chloro-5-(trifluoromethyl)phenyl]-N-[2,4-dinitro-6-(trifluoromethyl)phenyl]aminothio]-N-methyl-2-naphthalenesulfonamide | 100 |
| N-[N-[2-chloro-5-(trifluoromethyl)phenyl]-N-[2,4-dinitro-6-(trifluoromethyl)phenylaminothio]-N-butyl-N',N'-dimethylsulfamide | 100 |
| untreated check | 0 |

EXAMPLE 15

Eggs of the beet armyworm (*Spodoptera exigua*), laid on cellophane discs each containing 50–75 eggs, were placed in petri dishes and lightly sprayed with 200 ppm concentration of the indicated compounds in acetone solution. Three days later, percent control (% eggs failing to hatch) was determined.

| Compounds | % Control |
|---|---|
| N-[N-(2-chloro-5-trifluoromethyl)-N-(2,4-dinitro-6-trifluoromethylphenyl)-aminothio]-N-(2-methoxyethyl)-4-methyl-benzenesulfonamide | 100 |
| 4-chloro-N-[N-(2-chloro-5-trifluoromethyl-phenyl)-N-(2,4-dinitro-6-trifluoro-methylphenyl)aminothio]-N-methylben-zenesulfonamide | 100 |
| N-butyl-N-[N-[2-chloro-5-(trifluoro-methyl)phenyl]-N-[2,4-dinitro-6-(trifluoromethyl)phenyl]aminothio]-4-methylbenzenesulfonamide | 100 |
| N-butyl-N-[N-[2-chloro-5-(trifluoro-methyl)phenyl]-N-[2,4-dinitro-6-(trifluoromethyl)phenyl]aminothio]-benzenesulfonamide | 100 |
| untreated check | 0 |

EXAMPLE 16

Twenty-five newly hatched mosquito larvae were placed in 25 ml of distilled water in 4 oz glass jars, and 10 mg diet, consisting of 2 parts liver powder and 1 part brewer's yeast, was added. The test compound, N-[N-(2-chloro-5-(trifluoromethyl)phenyl]-N-[2,4-dinitro-6-(trifluoromethyl)phenyl]aminothio]-N,4-dimethylben-zenesulfonamide, dissolved in 0.2 ml acetone, was added to the jars to give a final concentration of 0.5 ppm. Triplicate runs were made. The jars were capped and held at 27°–30° under continuous light. Additional diet was added to each jar as follows: day 3, 20 mg diet; each succeeding day, a slight sprinkling of diet to replace that eaten. The number of dead insects were recorded daily. The test was terminated when all insects had died or become pupae. The efficacy of the test compound was determined by calculation of the $EC_{50}$ value, which is defined as the concentration at which 50% of the initial larvae fail to become adults. The $EC_{50}$ for the test compound was found to be 0.00081 ppm.

EXAMPLE 17

Stems of nasturtium leaves infested with bean aphids (*Aphis fabae*) were placed in individual vials of water. The leaves were sprayed to run-off with a series of suspensions of N-[N-[2-chloro-5-(trifluoromethyl)-phenyl]-N-[2,4-dinitro-6-(trifluoromethyl)-phenyl-]aminothio]-N,4-dimethylbenzenesulfonamide. Suspensions were prepared by dissolving 50 mg of the compound in 10 ml of acetone, adding 1 ml of 1% methocel 15, and diluting to volume with Duponol ®:water at 1:3000. Evaluations with respect to % kill 24 hours later are set forth below.

| % Spray Concentration | 24 Hours Evaluation (% Kill) |
|---|---|
| 0.1 | 100 |
| 0.005 | 100 |
| untreated check | 0 |

EXAMPLE 18

Five adult cotton boll weevils (*Anthonomus grandis*) were confined in a 4-oz. wide mouth jar. These were sprayed with a 1% acetone solution of the indicated compounds. Percent mortality after 24 hours is set forth below.

| Compounds | % Mortality |
|---|---|
| N-butyl-N-[N-[2-chloro-5-(trifluoro-methyl)phenyl]-N-[2,4-dinitro-6-(trifluoromethyl)phenyl]aminothio]-2-methylbenzenesulfonamide | 100 |
| N-[2-chloro-5-(trifluoromethyl)phenyl]-N-[2,4-dinitro-6-(trifluoromethyl)-phenyl]-2-oxo-1-pyrrolidinesulfen-amide | 100 |
| N-[N-[2-chloro-5-(trifluoromethyl)-phenyl]-N-[2,4-dinitro-6-(trifluoro-methyl)phenyl]aminothio]-N-methyl-2-naphthalenesulfonamide | 100 |
| N-[N-[2-chloro-5-(trifluoromethyl)-phenyl]-N-[2,4-dinitro-6-(trifluoro-methyl)phenyl]aminothio]-N-butyl-N',N'-dimethylsulfamide | 100 |
| N-butyl-N-[N-[2-chloro-5-(trifluoro-methyl)phenyl]-N-[2,4-dinitro-6-(trifluoromethyl)phenyl]aminothio]-4-methylbenzenesulfonamide | 100 |
| N-butyl-N-[N-[2-chloro-5-(trifluoro-methyl)phenyl]-N-[2,4-dinitro-6-(trifluoromethyl)phenyl]aminothio]-benzenesulfonamide | 100 |
| untreated check | 0 |

EXAMPLE 19

Twenty adult houseflies were confined in each of several cylindrical stainless steel cages (7.5 cm D×4 cm high) with wire screens of the ends. These were sprayed with 1% acetone solutions of the indicated compounds. Percent mortality after 24 hours are as follows:

| Compounds | % Mortality |
|---|---|
| N-butyl-N-[N-[2-chloro-5-(trifluoro-methyl)phenyl]-N-[2,4-dinitro-6-(trifluoromethyl)phenyl]aminothio]-2-methylbenzenesulfonamide | 100 |
| N-[2-chloro-5-(trifluoromethyl)phenyl]-N-[2,4-dinitro-6-(trifluoromethyl)-phenyl]-2-oxo-1-pyrrolidinesulfenamide | 100 |
| N-[N-[2-chloro-5-(trifluoromethyl)phenyl]-N[2,4-dinitro-6-(trifluoromethyl)-phenyl]aminothio]-N-methyl-2-naphtha-lenesulfonamide | 100 |
| N-[N-[2-chloro-5-(trifluoromethyl)-phenyl]-N-[2,4-dinitro-6-(trifluoro-methyl)phenyl]aminothio]-N-butyl-N',N'-dimethylsulfamide | 100 |
| N-butyl-N-[N-[2-chloro-5-(trifluoro-methyl)phenyl]-N-[2,4-dinitro-6-(trifluoromethyl)phenyl]aminothio]-4-methylbenzenesulfonamide | 100 |
| N-butyl-N-[N-[2-chloro-5-(trifluoro-methyl)phenyl]-N-[2,4-dinitro-6-(trifluoromethyl)phenyl]aminothio]-benzenesulfonamide | 100 |
| untreated check | 0 |

EXAMPLE 20

Five red-legged grasshoppers (*Melanoplus femurru-brum*) were confined in each of several cylindrical stainless steel cages (7.5 cm D×4 cm high) with wire screens at the end. These were sprayed with 10 ppm concentration of the indicated compounds in acetone solution. Percent mortality after 48 hours is recorded below.

| Compounds | % Mortality |
|---|---|
| N-butyl-N-[N-[2-chloro-5-(trifluoromethyl)phenyl]-N-[2,4-dinitro-6-(trifluoromethyl)phenyl]aminothio]-4-methylbenzenesulfonamide | 100 |
| N-butyl-N-[N-[2-chloro-5-(trifluoromethyl)phenyl]-N-[2,4-dinitro-6-(trifluoromethyl)phenyl]aminothio]benzenesulfonamide | 100 |
| untreated check | 0 |

For the control of anthropod pests of animals, compounds of this invention are generally applied to the locus of infestation, to the area to be protected or to the pests themselves. Effective compounds to be applied depend on the specific compound used, the species to be controlled, its life cycle, its size and location, the amount of rainfall, the time of year, moisture, temperature, type of application and other variables. In general, 0.001% to 10% solutions, dispersions, dusts, etc. may be required for anthropod control in these areas, with rates of 0.05% to 5% solution usually being sufficient in many situations. In efficient large scale operations, rates in the range of 0.01% to 2.5% solution are generally used.

EXAMPLE 21

Four-ounce wide mouth jars, each containing 10 brown dog ticks (*Rhipicephalus sanguineus*), were sprayed with 12.5 ppm concentration of the indicated compounds in acetone solution. The ticks were confined with caps which were also sprayed. Forty eight hours later, percent mortality was determined.

| Compounds | % Mortality |
|---|---|
| N-butyl-N-[N-[2-chloro-5-(trifluoromethyl)phenyl]-N-[2,4-dinitro-6-(trifluoromethyl)phenyl]aminothio]-4-methylbenzenesulfonamide | 100 |
| N-butyl-N-[N-[2-chloro-5-(trifluoromethyl)phenyl]-N-[2,4-dinitro-6-(trifluoromethyl)phenyl]aminothio]benzenesulfonamide | 100 |

The compounds of this invention are also useful as plant disease control agents. They are effective for the control of a broad spectrum of plant diseases as represented by, but not limited to, soil-borne fungal pathogens *Rhizoctonia solani* and *Pythium* sp., foliar pathogens, *Puccinia graminis*, *Erisyphe cichoracearum*, *Venturia inaequalis* and *Phytophthora infestans*, fruit and vegetable rotting fungi, *Sclerotinia sclerotiorum* and *Rhizopus stolonifer* and the seedborne fungus *Helminthosporium oryzae*. Diseases of a wide variety of ornamental, vegetable, cereal and fruit crops are controlled by the compounds of this invention.

Disease control is accomplished by applying the compound to the portion of the plant to be protected, such as the roots, stems, foliage, fruit, seeds, tubers or bulbs, or to the media (soil or sand) in which the plants to be protected are growing. The compound may also be applied to the seed from which the plants to be protected are to be grown.

Rates of application for these compounds will be influenced by many factors of the environment and must be determined under use conditions. Foliage can normally be protected when treated at a rate of from 1 to 500 ppm of active ingredient. Plants growing in soil treated at a concentration of from 0.1 to about 20 kg/ha can be protected from disease. Seed and seedlings can normally be protected when seed is treated at a rate of from 0.06 to about 3 grams per kilogram of seed.

EXAMPLE 22

Rice seed infected with *Helminthosporium oryzae* are treated with compounds of this invention at a rate of 1.3 g per kilogram of seed. This is accomplished by soaking infected seed for 1 minute in a suspension of the indicated compound dissolved in a solution containing 4% glycerine, 4% water, 0.02% Tween ®20, and 92% acetone. Treated seed are placed on moist blotters and enclosed in plastic bags for 18 days at which time disease ratings are made based on percent germination. As shown in the following table, compounds of this invention provided excellent disease control, as treated seed had a high percentage germination in contrast to untreated seed which did not germinate. Phytotoxicity in the form of growth reduction was observed on germinated seedlings in association with disease control.

| Compound | % Control of rice Helminthosporium in a seed treatment test |
|---|---|
| N-[N-[2-chloro-5-(trifluoromethyl)phenyl]-N-[2,4-dinitro-6-(trifluoromethyl)phenyl]aminothio]-N,4-dimethylbenzenesulfonamide | 70(G) |
| N-butyl-N-[N-[2-chloro-5-(trifluoromethyl)phenyl]-N-[2,4-dinitro-6-(trifluoromethyl)phenyl]aminothio]-2-methylbenzenesulfonamide | 70(G) |
| N-[N-[2-chloro-5-(trifluoromethyl)phenyl]-N-[2,4-dinitro-6-(trifluoromethyl)phenyl]aminothio]-4-methyl-N-(1-methylethyl)-benzenesulfonamide | 70(G) |
| N-butyl-N-[N-[2-chloro-5-(trifluoromethyl)phenyl]-N-[2,4-dinitro-6-(trifluoromethyl)phenyl]aminothio]-4-methylbenzenesulfonamide | 40(G) |
| N-butyl-N-[N-[2-chloro-5-(trifluoromethyl)phenyl]-N-[2,4-dinitro-6-(trifluoromethyl)phenyl]aminothio]benzenesulfonamide | 20(G) |
| N-[N-[2-chloro-5-(trifluoromethyl)phenyl]-N-[2,4-dinitro-6-(trifluoromethyl)phenyl]aminothio]-N-(4-methylphenylsulfonyl)glycine methyl ester | 60(G) |
| N-[N-[2,4-dinitro-6-(trifluoromethyl)phenyl]-N-(2,4,6-trifluorophenyl)aminothio]-N,4-dimethylbenzenesulfonamide | 90(G) |
| N-[2-chloro-5-(trifluoromethyl)phenyl]-N-[2,4-dinitro-6-(trifluoromethyl)phenyl]-2-oxo-1-pyrrolidinesulfenamide | 80(G) |
| N-[N-[2-chloro-5-(trifluoromethyl)phenyl]-N-[2,4-dinitro-6-(trifluoromethyl)phenyl]aminothio]-N-methyl-2-naphthalenesulfonamide | 100 (G) |
| N-[N-[2-chloro-5-(trifluoromethyl)phenyl]-N-[2,4-dinitro-6-(trifluoromethyl)phenyl]aminothio]-N-butyl-N',N'-dimethylsulfamide | 80(G) |

*G = growth reduction

EXAMPLE 23

Pythium infested soil was placed in a 900 cc cup. Compounds of this invention were mixed at a rate of 1.5 kg/ha in a section 2" wide×2" deep×4" long to simulate an in-the-row application. Five cotton seeds were planted in the treated soil. After 8 days, the cotton plants were removed and rated for disease control. Phytotoxicity in the form of growth reduction was observed on some of the plants in association with disease control.

| Compounds | % control Pythium |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 0(G) |
| N-butyl-N-[N-[2-chloro-5-(trifluoromethyl)-phenyl]-N-[2,4-dinitro-6-(trifluoromethyl)-phenyl]aminothio]-4-methylbenzenesulfonamide | 0(G) |
| N-[N-[2-chloro-5-(trifluoromethyl)phenyl]-N-[2,4-dinitro-6-(trifluoromethyl)phenyl]-N-(4-methylphenylsulfonyl)glycine methyl ester | 50 |
| N-[N-[2,4-dinitro-6-(trifluoromethyl)phenyl]-N-(2,4,6-trifluorophenyl)aminothio]-N,4-dimethylbenzenesulfonamide | 100(G) |
| N-[2-chloro-5-(trifluoromethyl)phenyl]-N-[2,4-dinitro-6-(trifluoromethyl)phenyl]-2-oxo-1-pyrrolidinesulfenamide | 50 |
| N-[N-[2-chloro-5-(trifluoromethyl)phenyl]-N-[2,4-dinitro-6-(trifluoromethyl)phenyl]-aminothio]-N-methyl-2-naphthalenesulfonamide | 0 |
| N-[N-[2-chloro-5-(trifluoromethyl)phenyl]-N-[2,4-dinitro-6-(trifluoromethyl)phenyl]-aminothio]-N-butyl-N',N'-dimethylsulfamide | 0 |

*G = growth reduction

EXAMPLE 24

*Rhizoctonia solani*-infested soil was placed in a 900 cc cup. Compounds of this invention were mixed at a rate of 1.5 kg/ha in a section 2" wide×2" deep×4" long to simulate an in-the-row application. Five cotton seeds were planted in the treated soil. After 8 days, the cotton plants were removed and rated for disease control. Phytotoxicity in the form of growth reduction was observed on some of the plants in association with disease control.

| Compounds | % Rhizoctonia solani control |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 100(G) |
| N-butyl-N-[N-[2-chloro-5-(trifluoromethyl)-phenyl]-N-[2,4-dinitro-6-(trifluoromethyl)-phenyl]aminothio]-2-methylbenzenesulfonamide | 50 |
| N-butyl-N-[N-[2-chloro-5-(trifluoromethyl)-phenyl]-N-[2,4-dinitro-6-(trifluoromethyl)-phenyl]aminothio]-4-methylbenzenesulfonamide | 100(G) |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 50 |
| N-[N-[2,4-dinitro-6-(trifluoromethyl)phenyl]-N-(2,4,6-trifluorophenyl)aminothio]-N,4-dimethylbenzenesulfonamide | 70 |
| N-[2-chloro-5-(trifluoromethyl)phenyl]-N-[2,4-dinitro-6-(trifluoromethyl)phenyl]-2-oxo-1-pyrrolidinesulfenamide | 90 |
| N-[N-[2-chloro-5-(trifluoromethyl)phenyl]-N-[2,4-dinitro-6-(trifluoromethyl)phenyl]-aminothio]-N-methyl-2-naphthalenesulfonamide | 0 |
| N-[N-[2-chloro-5-(trifluoromethyl)phenyl]-N-[2,4-dinitro-6-(trifluoromethyl)phenyl]-aminothio]-N-butyl-N',N'-dimethyl-sulfamide | 0 |

*G = growth reduction

EXAMPLE 25

Compounds of this invention are dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on apple seedlings. The following day, the plants are inoculated with a spore suspension of the fungus *Venturia inaequalis* and incubated in a growth room for 10–12 days. Disease ratings are then made. As shown in the following table, most of the compounds of this invention provided excellent disease control, as treated plants had little or no apple scab lesions in contrast to untreated plants which were covered with scab lesions. Phytotoxicity in the form of foliar burn was observed on some of the plants in association with disease control.

| Compounds | % control of apple scab in a preventive test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | -(B) |
| N-butyl-N-[N-[2-chloro-5-(trifluoromethyl)-phenyl]-N-[2,4-dinitro-6-(trifluoromethyl)-phenyl]aminothio]-2-methylbenzenesulfonamide | 100 |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 100(B) |
| N-butyl-N-[N-[2-chloro-5-(trifluoromethyl)-phenyl]-N-[2,4-dinitro-6-(trifluoromethyl)-phenyl]aminothio]-4-methylbenzenesulfonamide | 75 |
| N-butyl-N-[N-[2-chloro-5-(trifluoromethyl)-phenyl]-N-[2,4-dinitro-6-(trifluoromethyl)-phenyl]aminothio]benzenesulfonamide | 100 |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 0 |
| N-[N-[2,4-dinitro-6-(trifluoromethyl)phenyl]-N-(2,4,6-trifluorophenyl)aminothio]-N,4-dimethylbenzenesulfonamide | 100(B) |
| N-[2-chloro-5-(trifluoromethyl)phenyl]-N-[2,4-dinitro-6-(trifluoromethyl)phenyl]-2-oxo-1-pyrrolidinesulfenamide | -(B) |
| N-[N-[2-chloro-5-(trifluoromethyl)phenyl]-N-[2,4-dinitro-6-(trifluoromethyl)phenyl]-aminothio]-N-methyl-2-naphthalenesulfonamide | 50(B) |
| N-[N-[2-chloro-5-(trifluoromethyl)phenyl]-N-[2,4-dinitro-6-(trifluoromethyl)phenyl]-aminothio]-N-butyl-N',N'-dimethylsulfamide | 100(B) |

*B = burn

EXAMPLE 26

Compounds of this invention are dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on apple seedlings. The following day, ½ inch of simulated rainfall is applied to the foliage of the plants. When the foliage is dry, the plants are inoculated with a spore suspension of the fungus *Venturia inaequalis* and incubated in a growth room for 10–12 days. Disease ratings are then made. As shown in the following table, most of the compounds of this invention provided excellent disease control, as treated plants had little or no apple scab lesions in contrast to untreated plants which were covered with scab lesions. Phytotoxicity in the form of foliar burn was observed on the plants in association with disease control.

| Compounds | % control of apple scab in a residual wash-off test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 100(B) |
| N-butyl-N-[N-[2-chloro-5-(trifluoromethyl)phenyl]-N-[2,4-dinitro-6-(trifluoromethyl)phenyl]aminothio]-2-methylbenzenesulfonamide | 100(B) |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 100(B) |
| N-butyl-N-[N-[2-chloro-5-(trifluoromethyl)phenyl]-N-[2,4-dinitro-6-(trifluoromethyl)phenyl]aminothio]-4-methylbenzenesulfonamide | 100(B) |
| N-butyl-N-[N-[2-chloro-5-(trifluoromethyl)phenyl]-N-[2,4-dinitro-6-(trifluoromethyl)phenyl]aminothio]benzenesulfonamide | 100(B) |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 0 |
| N-[N-[2,4-dinitro-6-(trifluoromethyl)phenyl]-N-(2,4,6-trifluorophenyl)aminothio]-N,4-dimethylbenzenesulfonamide | 100(B) |
| N-[2-chloro-5-(trifluoromethyl)phenyl]-N-[2,4-dinitro-6-(trifluoromethyl)phenyl]-2-oxo-1-pyrrolidinesulfenamide | 75(B) |
| N-[N-[2-chloro-5-(trifluoromethyl)phenyl]-N-[2,4-dinitro-6-(trifluoromethyl)phenyl]aminothio]-N-methyl-2-naphthalenesulfonamide | 100(B) |
| N-[N-[2-chloro-5-(trifluoromethyl)phenyl]-N-[2,4-dinitro-6-(trifluoromethyl)phenyl]aminothio]-N-butyl-N',N'-dimethylsulfamide | 100(B) |

*B = burn

EXAMPLE 27

Compounds of this invention are dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on apple seedlings. When the foliage is dry, the plants are exposed to 3500 foot candles of light from a xenon arc source for a period of 16 hours. This light source approximates the spectrum of natural sunlight, and is used to assess photostability of the compounds of this invention on plant foliage. The following day, the plants are inoculated with a spore suspension of the fungus *Venturia inaequalis* and incubated in a growth room for 10–12 days. Disease ratings are then made. As shown in the following table, most of the compounds of this invention provided excellent disease control, as some of the treated plants had little or no apple scab lesions in contrast to untreated plants which were covered with scab lesions. Phytotoxicity in the form of foliar burn was observed on some of the plants in association with disease control.

| Compounds | % control apple scab in a photo-stability test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 100 |
| N-butyl-N-[N-[2-chloro-5-(trifluoromethyl)phenyl]-N-[2,4-dinitro-6-(trifluoromethyl)phenyl]aminothio]-2-methylbenzenesulfonamide | 80 |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 0 |
| N-butyl-N-[N-[2-chloro-5-(trifluoromethyl)phenyl]-N-[2,4-dinitro-6-(trifluoromethyl)phenyl]aminothio]-4-methylbenzenesulfonamide | 0 |
| N-butyl-N-[N-[2-chloro-5-(trifluoromethyl)phenyl]-N-[2,4-dinitro-6-(trifluoromethyl)phenyl]aminothio]benzenesulfonamide | 0 |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 0 |
| N-[N-[2,4-dinitro-6-(trifluoromethyl)phenyl]-N-(2,4,6-trifluorophenyl)aminothio]-N,4-dimethylbenzenesulfonamide | 80 |
| N-[2-chloro-5-(trifluoromethyl)phenyl]-N-[2,4-dinitro-6-(trifluoromethyl)phenyl]-2-oxo-1-pyrrolidinesulfenamide | 50(B) |
| N-[N-[2-chloro-5-(trifluoromethyl)phenyl]-N-[2,4-dinitro-6-(trifluoromethyl)phenyl]aminothio]-N-methyl-2-naphthalenesulfonamide | 0 |
| N-[N-[2-chloro-5-(trifluoromethyl)phenyl]-N-[2,4-dinitro-6-(trifluoromethyl)phenyl]aminothio]-N-butyl-N',N'-dimethylsulfamide | 0 |

*B = burn

EXAMPLE 28

Compounds of this invention are dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on cucumber seedlings. The following day, the plants are inoculated with a spore suspension of the fungus *Erysiphe cichoracearum* and incubated in a growth room for 7 days. Disease ratings are then made. As shown in the following table, most of the compounds of this invention provided excellent disease control, as treated plants had little or no powdery mildew in contrast to untreated plants which were covered with powdery mildew. Phytotoxicity in the form of foliar burn or growth reduction was observed on some of the plants in association with disease control.

| Compound | % control cucumber powdery mildew in a preventive test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 100 |
| N-butyl-N-[N-[2-chloro-5-(trifluoromethyl)phenyl]-N-[2,4-dinitro-6-(trifluoromethyl)phenyl]aminothio]-2-methylbenzenesulfonamide | 100 |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 100 |
| N-butyl-N-[N-[2-chloro-5-(trifluoromethyl)phenyl]-N-[2,4-dinitro-6-(trifluoromethyl)phenyl]aminothio]-4-methylbenzenesulfonamide | 100 |
| N-butyl-N-[N-[2-chloro-5-(trifluoromethyl)phenyl]-N-[2,4-dinitro-6-(trifluoromethyl)phenyl]aminothio]benzenesulfonamide | 100 |

| Compound | % control cucumber powdery mildew in a preventive test |
|---|---|
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 0 |
| N-[N-[2,4-dinitro-6-(trifluoromethyl)phenyl]-N-(2,4,6-trifluorophenyl)aminothio]-N,4-dimethylbenzenesulfonamide | 100 |
| N-[2-chloro-5-(trifluoromethyl)phenyl]-N-[2,4-dinitro-6-(trifluoromethyl)phenyl]-2-oxo-1-pyrrolidinesulfenamide | 100(B) |
| N-[N-[2-chloro-5-(trifluoromethyl)phenyl]-N-[2,4-dinitro-6-(trifluoromethyl)phenyl]-aminothio]-N-methyl-2-naphthalenesulfonamide | 100 |
| N-[N-[2-chloro-5-(trifluoromethyl)phenyl]-N-[2,4-dinitro-6-(trifluoromethyl)phenyl]-aminothio]-N-butyl-N',N'-dimethylsulfamide | 100(G) |

*B = burn and G = growth reduction

EXAMPLE 29

Cucumber plants are inoculated with a spore suspension of the fungus *Erisyphe cichoracearum* and in a growth room overnight. The following day, the plants are sprayed to the point of run-off with a suspension prepared by dissolving compounds of this invention in acetone in an amount equal to 6% of the final volume and then suspended at a concentration of 20 ppm in purified water containing 25 ppm of the surfactant Alkanol® XC (sodium alkyl naphthalene sulfonate). Plants are returned to the growth room for an additional 6 days when disease ratings are then made. As shown in the following table, most of the compounds of this invention provided excellent disease control, as treated plants had little or no powdery mildew in contrast to untreated plants which were covered with powdery mildew. Phytotoxicity in the form of foliar burn or growth reduction was observed on some of the plants in association with disease control.

| Compound | % control of cucumber powdery mildew in a curative test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 100 |
| N-butyl-N-[N-[2-chloro-5-(trifluoromethyl)-phenyl]-N-[2,4-dinitro-6-(trifluoromethyl)-phenyl]aminothio]-2-methylbenzenesulfonamide | 93 |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 90 |
| N-butyl-N-[N-[2-chloro-5-(trifluoromethyl)-phenyl]-N-[2,4-dinitro-6-(trifluoromethyl)-phenyl]aminothio]-4-methylbenzenesulfonamide | 92(G) |
| N-butyl-N-[N-[2-chloro-5-(trifluoromethyl)-phenyl]-N-[2,4-dinitro-6-(trifluoromethyl)-phenyl]aminothio]benzenesulfonamide | 50(G) |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 0 |
| N-[N-[2,4-dinitro-6-(trifluoromethyl)phenyl]-N-(2,4,6-trifluorophenyl)aminothio]-N,4-dimethylbenzenesulfonamide | 99(G) |
| N-[2-chloro-5-(trifluoromethyl)phenyl]-N-[2,4-dinitro-6-(trifluoromethyl)phenyl]-2-oxo-1-pyrrolidinesulfenamide | 100(B) |
| N-[N-[2-chloro-5-(trifluoromethyl)phenyl]-N-[2,4-dinitro-6-(trifluoromethyl)phenyl]-aminothio]-N-methyl-2-naphthalenesulfonamide | 50 |
| N-[N-[2-chloro-5-(trifluoromethyl)phenyl]-N-[2,4-dinitro-6-(trifluoromethyl)phenyl]-aminothio]-N-butyl-N',N'-dimethylsulfamide | 99(G) |

*B = burn and
G = growth reduction

EXAMPLE 30

Compounds of this invention are dissolved in acetone in an amount equal to 6% of the final volume and then suspended at a concentration of 20 ppm in purified water containing 25 ppm of the surfactant Alkanol® XC (sodium alkyl naphthalene sulfonate). This suspension is sprayed to the point of run-off on cucumber seedlings. The following day, ½ inch of simulated rainfall is applied to the foliage of the plants. When the foliage is dry, the plants are inoculated with a spore suspension on the fungus *Erysiphe cichoracearum* and incubated in a growth room for 7 days. Disease ratings are then made. As shown in the following table, most of the compounds of this invention provided excellent disease control, as treated plants had little or no powdery mildew in contrast to untreated plants where were covered with powdery mildew.

| Compounds | % control cucumber powdery mildew in a residual wash-off test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 92 |
| N-butyl-N-[N-[2-chloro-5-(trifluoromethyl)-phenyl]-N-[2,4-dinitro-6-(trifluoromethyl)-phenyl]aminothio]-2-methylbenzenesulfonamide | 100 |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 99 |
| N-butyl-N-[N-[2-chloro-5-(trifluoromethyl)-phenyl]-N-[2,4-dinitro-6-(trifluoromethyl)-phenyl]aminothio]-4-methylbenzenesulfonamide | 100 |
| N-butyl-N-[N-[2-chloro-5-(trifluoromethyl)-phenyl]-N-[2,4-dinitro-6-(trifluoromethyl)-phenyl]aminothio]benzenesulfonamide | 98 |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 0 |
| N-[N-[2,4-dinitro-6-(trifluoromethyl)phenyl]-N-(2,4,6-trifluorophenyl)aminothio]-N,4-dimethylbenzenesulfonamide | 100 |
| N-[2-chloro-5-(trifluoromethyl)phenyl]-N-[2,4-dinitro-6-(trifluoromethyl)phenyl]-2-oxo-1-pyrrolidinesulfenamide | 30 |
| N-[N-[2-chloro-5-(trifluoromethyl)phenyl]-N-[2,4-dinitro-6-(trifluoromethyl)phenyl]-aminothio]-N-methyl-2-naphthalenesulfonamide | 85 |
| N-[N-[2-chloro-5-(trifluoromethyl)phenyl]-N-[2,4-dinitro-6-(trifluoromethyl)phenyl]-aminothio]-N-butyl-N',N'-dimethylsul- | |

| Compounds | % control cucumber powdery mildew in a residual wash-off test |
|---|---|
| famide | 98 |

EXAMPLE 31

Compounds of this invention are dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off in cucumber seedlings. When the foliage is dry, the plants are exposed to 3500 foot candles of light from a xenon arc source for a period of 16 hours. This light source approximates the spectrum of natural sunlight, and is used to assess photostability of the compounds of this invention on plant foliage. The following day, the plants are inoculated with a spore suspension of the fungus *Erysiphe cichoracearum* and incubated in a growth room for 7 days. Disease ratings are then made. As shown in the following table, most of the compounds of this invention provided excellent disease control, as treated plants had little or no powdery mildew in contrast to untreated plants which were covered with powdery mildew.

| Compounds | % control of cucumber powdery mildew in a photo-stability test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 0 |
| N-butyl-N-[N-[2-chloro-5-(trifluoromethyl)-phenyl]-N-[2,4-dinitro-6-(trifluoromethyl)-phenyl]aminothio]-2-methylbenzenesulfonamide | 100 |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 40 |
| N-butyl-N-[N-[2-chloro-5-(trifluoromethyl)-phenyl]-N-[2,4-dinitro-6-(trifluoromethyl)-phenyl]aminothio]-4-methylbenzenesulfonamide | 75 |
| N-butyl-N-[N-[2-chloro-5-(trifluoromethyl)-phenyl]-N-[2,4-dinitro-6-(trifluoromethyl)-phenyl]aminothio]benzenesulfonamide | 0 |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 0 |
| N-[N-[2,4-dinitro-6-(trifluoromethyl)phenyl]-N-(2,4,6-trifluorophenyl)aminothio]-N,4-dimethylbenzenesulfonamide | 100 |
| N-[2-chloro-5-(trifluoromethyl)phenyl]-N-[2,4-dinitro-6-(trifluoromethyl)phenyl]-2-oxo-1-pyrrolidinesulfenamide | 97 |
| N-[N-[2-chloro-5-(trifluoromethyl)phenyl]-N-[2,4-dinitro-6-(trifluoromethyl)phenyl]-aminothio]-N-methyl-2-naphthalenesulfonamide | 75 |
| N-[N-[2-chloro-5-(trifluoromethyl)phenyl]-N-[2,4-dinitro-6-(trifluoromethyl)phenyl]-aminothio]-N-butyl-N',N'-dimethysulfamide | 80 |

EXAMPLE 32

Compounds of this invention were dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on wheat seedlings. The following day, the plants are inoculated with a spore suspension of *Puccinia graminis* var. tritici and incubated in a saturated humidity chamber at 20° C. for 24 hours and then in a growth room for an additional 7 days, when disease ratings were made. As shown in the following table, most of the compounds of this invention provided excellent disease control. Treated plants had few or no rust pustules while the untreated plants had numerous rust pustules on each leaf. Phytotoxicity in the form of foliar burn was observed on some of the plants in association with disease control.

| Compounds | % control wheat rust in preventive test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 80 |
| N-butyl-N-[N-[2-chloro-5-(trifluoromethyl)-phenyl]-N-[2,4-dinitro-6-(trifluoromethyl)-phenyl]aminothio]-2-methylbenzenesulfonamide | 100 |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 100 |
| N-butyl-N-[N-[2-chloro-5-(trifluoromethyl)-phenyl]-N-[2,4-dinitro-6-(trifluoromethyl)-phenyl]aminothio]-4-methylbenzenesulfonamide | 100 |
| N-butyl-N-[N-[2-chloro-5-(trifluoromethyl)-phenyl]-N-[2,4-dinitro-6-(trifluoromethyl)-phenyl]aminothio]benzenesulfonamide | 100 |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 30 |
| N-[N-[2,4-dinitro-6-(trifluoromethyl)phenyl]-N-(2,4,6-trifluorophenyl)aminothio]N,4-dimethylbenzensulfonamide | 100 |
| N-[2-chloro-5-(trifluoromethyl)phenyl]-N-[2,4-dinitro-6-(trifluoromethyl)phenyl]-2-oxo-1-pyrrolidinesulfenamide | 100 |
| N-[N-[2-chloro-5-(trifluoromethyl)phenyl]-N-[2,4-dinitro-6-(trifluoromethyl)phenyl]-aminothio]-N-methyl-2-naphthalenesulfonamide | 100(B) |
| N-[N-[2-chloro-5-(trifluoromethyl)phenyl]-N-[2,4-dinitro-6-(trifluoromethyl)phenyl]-aminothio]-N-butyl-N'N'-dimethylsulfamide | 100 |

*B = burn

EXAMPLE 33

Compounds of this invention were dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on wheat seedlings. The following day, ½ inch of simulated rainfall is applied to the foliage of the plants. When the foliage is dry, the plants are inoculated with a spore suspension of *Puccinia graminis* var. tritici and incubated in a saturated humidity chamber at 20° C. for 24 hours and then in a growth room for an additional 7 days, when disease ratings were made. As shown in the following table, most of the compounds of this invention provided excellent disease control. Treated plants had few or no rust pustules while the untreated plants had numerous rust pustules on each leaf.

| Compounds | % control wheat rust in residual wash-off test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 100 |
| N-butyl-N-[N-[2-chloro-5-(trifluoromethyl)phenyl]-N-[2,4-dinitro-6-(trifluoromethyl)phenyl]aminothio]-2-methybenzenesulfonamide | 100 |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 97 |
| N-butyl-N-[N-[2-chloro-5-(trifluoromethyl)phenyl]-N-[2,4-dinitro-6-(trifluoromethyl)phenyl]aminothio]-4-methylbenzenesulfonamide | 100 |
| N-butyl-N-[N-[2-chloro-5-(trifluoromethyl)phenyl]-N-[2,4-dinitro-6-(trifluoromethyl)phenyl]aminothio]benzenesulfonamide | 97 |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 25 |
| N-[N-[2,4-dinitro-6-(trifluoromethyl)phenyl]-N-(2,4,6,-trifluorophenyl)aminothio]-N,4-dimethylbenzenesulfonamide | 97 |
| N-[2-chloro-5-(trifluoromethyl)phenyl]-N-[2,4-dinitro-6-(trifluoromethyl)phenyl]-2-oxo-1-pyrrolidinesulfenamide | 100 |
| N-[N-[2-chloro-5-(trifluoromethyl)phenyl]-N-[2,4-dinitro-6-(trifluoromethyl)phenyl]-aminothio]-N-methyl-2-naphthalenesulfonamide | 100 |
| N-[N-[2-chloro-5-(trifluoromethyl)phenyl]-N-[2,4-dinitro-6-(trifluoromethyl)phenyl]-aminothio]-N-butyl-N',N'-dimethylsulfamide | 90 |

EXAMPLE 34

Compounds of this invention were dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on wheat seedlings. When the foliage is dry, the plants are exposed to 3500 foot candles of light from a xenon arc source for a period of 16 hours. This light source approximates the spectrum of natural sunlight, and is used to assess photostability of the compounds of this invention on plant foliage. The following day, the plants are inoculated with a spore suspension of Puccinia graminis var. tritici and incubated in a saturated humidity chamber at 20° C. for 24 hours and then in a growth room for an additional 7 days, when disease ratings were made. As shown in the following table, most of the compounds of this invention provided excellent disease control. Treated plants had few or no rust pustules while the untreated plants had numerous rust pustules on each leaf. Phytotoxicity in the form of foliar burn was observed on some of the plants in association with disease control.

| Compounds | % control wheat rust in a photo-stability test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 40 |
| N-butyl-N-[N-[2-chloro-5-(trifluoromethyl)phenyl]-N-[2,4-dinitro-6-(trifluoromethyl)phenyl]aminothio]-2-methylbenzenesulfonamide | 98 |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 80(B) |
| N-butyl-N-[N-[2-chloro-5-(trifluoromethyl)phenyl]-N-[2,4-dinitro-6-(trifluoromethyl)phenyl]aminothio]-4-methylbenzenesulfonamide | 100 |
| N-butyl-N-[N-[2-chloro-5-(trifluoromethyl)phenyl]-N-[2,4-dinitro-6-(trifluoromethyl)phenyl]aminothio]benzenesulfonamide | 90 |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 20 |
| N-[N-[2,4-dinitro-6-(trifluoromethyl)phenyl]-N-(2,4,6-trifluorophenyl)aminothio]-N,4-dimethylbenzenesulfonamide | 70 |
| N-[2-chloro-5-(trifluoromethyl)phenyl]-N-[2,4-dinitro-6-(trifluoromethyl)phenyl]-2-oxo-1-pyrrolidinesulfenamide | 100 |
| N-[N-[2-chloro-5-(trifluoromethyl)phenyl]-N-[2,4-dinitro-6-(trifluoromethyl)phenyl]-aminothio]-N-methyl-2-naphthalenesulfonamide | 100(B) |
| N-[N-[2-chloro-5-(trifluoromethyl)phenyl]-N-[2,4-dinitro-6-(trifluoromethyl)phenyl]-aminothio]-N-butyl-N',N'-dimethylsulfamide | 80(B) |

*B = burn

EXAMPLE 35

Compounds of this invention are dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on tomato seedlings. The following day, the plants are inoculated with a spore suspension of the fungus Phytophthora infestans and incubated in a growth room for 4 days. Disease ratings are then made. As shown in the following table, several of the compounds of this invention provided excellent disease control, as treated plants had no late blight lesions in contrast to untreated plants which were covered with lesions. Phytotoxicity in the form of foliar burn was observed on some of the plants in association with disease control.

| Compounds | % control tomato late blight in a preventive test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | -(B) |
| N-butyl-N-[N-[2-chloro-5-(trifluoromethyl)phenyl]-N-[2,4-dinitro-6-(trifluoromethyl)phenyl]aminothio]-2-methylbenzenesulfonamide | -(B) |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | -(B) |
| N-butyl-N-[N-[2-chloro-5-(trifluoromethyl)phenyl]-N-[2,4-dinitro-6-(trifluoromethyl)phenyl]aminothio]-4-methylbenzenesulfonamide | 100(B) |

-continued

| Compounds | % control tomato late blight in a preventive test |
|---|---|
| N-butyl-N-[N-[2-chloro-5-(trifluoromethyl)-phenyl]-N-[2,4-dinitro-6-(trifluoromethyl)-phenyl]aminothio]benzenesulfonamide | -(B) |
| N-[N-[2-chloro-5-(trifluoromethyl)phenyl]-N-[2,4-dinitro-6-(trifluoromethyl)phenyl]-aminothio]-N-(4-methylphenylsulfonyl)glycine mether ester | 0 |
| N-[N-[2,4-dinitro-6-(trifluoromethyl)phenyl]-N-(2,4,6-trifluorophenyl)aminothio]-N,4-dimethylbenzenesulfonamide | 100 |
| N-[2-chloro-5-(trifluoromethyl)phenyl]-N-[2,4-dinitro-6-(trifluoromethyl)phenyl]-2-oxo-1-pyrrolidinesulfenamide | -(B) |
| N-[N-[2-chloro-5-(trifluoromethyl)phenyl]-N-[2,4-dinitro-6-(trifluoromethyl)phenyl]-aminothio]-N-methyl-2-naphthalenesulfonamide | -(B) |
| N-[N-[2-chloro-5-(trifluoromethyl)phenyl]-N-[2,4-dinitro-6-(trifluoromethyl)phenyl]-aminothio]-N-butyl-N',N'-dimethylsulfamide | -(B) |

*B = burn

EXAMPLE 36

Compounds of this invention are dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on tomato seedlings. The following day, ½ inch of simulated rainfall is applied to the foliage of the plants. When the foliage is dry, the plants are inoculated with a spore suspension of the fungus *Phytophthora infestans* and incubated in a growth room for 4 days. Disease ratings are then made. As shown in the following table, most of the compounds of this invention provided excellent disease control, as treated plants had little or no late blight lesions in contrast to untreated plants which were covered with lesions. Phytotoxicity in the form of foliar burn was observed on some of the plants in association with disease control.

| Compounds | % control tomato late blight in a residual wash-off test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 100(B) |
| N-butyl-N-[N-[2-chloro-5-(trifluoromethyl)-phenyl]-N-[2,4-dinitro-6-(trifluoromethyl)-phenyl]aminothio]-2-methylbenzenesulfonamide | -(B) |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 100(B) |
| N-butyl-N-[N-[2-chloro-5-(trifluoromethyl)-phenyl]-N-[2,4-dinitro-6-(trifluoromethyl)-phenyl]aminothio]-4-methylbenzenesulfonamide | 100(B) |
| N-butyl-N-[N-[2-chloro-5-(trifluoromethyl)-phenyl]-N-[2,4-dinitro-6-(trifluoromethyl)-phenyl]aminothio]benzenesulfonamide | 100(B) |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 0 |
| N-[N-[2,4-dinitro-6-(trifluoromethyl)phenyl]-N-(2,4,6-trifluorophenyl)aminothio]-N,4-dimethylbenzenesulfonamide | 100 |
| N-[2-chloro-5-(trifluoromethyl)phenyl]-N-[2,4-dinitro-6-(trifluoromethyl)phenyl]-2-oxo-1-pyrrolidinesulfenamide | 50(B) |
| N-[N-[2-chloro-5-(trifluoromethyl)phenyl]-N-[2,4-dinitro-6-(trifluoromethyl)phenyl]-aminothio]-N-methyl-2-naphthalenesulfonamide | 100(B) |
| N-[N-[2-chloro-5-(trifluoromethyl)phenyl]-N-[2,4-dinitro-6-(trifluoromethyl)phenyl]-aminothio]-N-butyl-N',N'-dimethylsulfamide | 93(B) |

*B = burn

EXAMPLE 37

Compounds of this invention are dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on tomato seedlings. When the foliage is dry, the plants are exposed to 3500 foot candles of light from a xenon arc source for a period of 16 hours. This light source approximates the spectrum of natural sunlight, and is used to assess photostability of the compounds of this invention on plant foliage. The following day, the plants are inoculated with a spore suspension of the fungus *Phytophthora infestans* and incubated in a growth room for 4 days. Disease ratings are then made. As shown in the following table, most of the compounds of this invention provided excellent disease control, as treated plants had little or no late blight lesions in contrast to untreated plants which were covered with lesions. Phytotoxicity in the form of foliar burn was observed on some of the plants in association with disease control.

| Compounds | % control tomato late blight in a photostability test |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 50(B) |
| N-butyl-N-[N-[2-chloro-5-(trifluoromethyl)-phenyl]-N-[2,4-dinitro-6-(trifluoromethyl)-phenyl]aminothio]-2-methylbenzenesulfonamide | 90(B) |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 90 |
| N-butyl-N-[N-[2-chloro-5-(trifluoromethyl)-phenyl]-N-[2,4-dinitro-6-(trifluoromethyl)-phenyl]aminothio]-4-methylbenzenesulfonamide | 95(B) |
| N-butyl-N-[N-[2-chloro-5-(trifluoromethyl)-phenyl]-N-[2,4-dinitro-6-(trifluoromethyl)-phenyl]aminothio]benzenesulfonamide | 90(B) |
| N-[N-[2-chloro-5-(trifluoromethyl)phenyl]-N-[2,4-dinitro-6-(trifluoromethyl)phenyl]-aminothio]-N-(4-methylphenylsulfonyl)glycine methyl ester | 0 |
| N-[N-[2,4-dinitro-6-(trifluoromethyl)phenyl]-N-(2,4,6-trifluorophenyl)aminothio]-N,4-dimethylbenzenesulfonamide | 100 |
| N-[2-chloro-5-(trifluoromethyl)phenyl]-N-[2,4-dinitro-6-(trifluoromethyl)phenyl]-2-oxo-1-pyrrolidinesulfenamide | -(B) |
| N-[N-[2-chloro-5-(trifluoromethyl)phenyl]- | |

-continued

| Compounds | % control tomato late blight in a photostability test |
|---|---|
| N-[2,4-dinitro-6-(trifluoromethyl)phenyl]-aminothio]-N-methyl-2-naphthalenesulfonamide | 100(B) |
| N-[N-[2-chloro-5-(trifluoromethyl)phenyl]-N-[2,4-dinitro-6-(trifluoromethyl)phenyl]-aminothio]-N-butyl-N',N'-dimethylsulfamide | 90(B) |

*B = burn

EXAMPLE 38

Compounds of this invention were dissolved in acetone in an amount equal to 6% of final volume and then suspended at a concentration of 100 ppm in purified water containing 500 ppm of the surfactant Alkanol ® XC (sodium alkyl naphthalene sulfonate). This solution was oversprayed on a Rhizopus-corn meal mixture in 6 cm aluminum cups. The sprayed plates were placed in a closed plastic bag, stored at 20° C. for 7 days, and then rated.

The untreated cups were completely covered with Rhizopus mycelial growth, but the treated cups were mostly free of growth by this disease-causing organism.

TABLE 5

| Compound | % control Rhizopus |
|---|---|
| N-butyl-N-[N-[2-chloro-5-(trifluoromethyl)phenyl]-N-[2,4-dinitro-6-(trifluoromethyl)phenyl]aminothio]-2-methylbenzenesulfonamide | 90 |
| N-[N-[2-chloro-5-(trifluoromethyl)phenyl]-N-[2,4-dinitro-5-(trifluoromethyl)phenyl]-aminothio]-4-methyl-N-(1-methylethyl)-benzenesulfonamide | 100 |

EXAMPLE 39

Surface-sterilized carrot sections were dipped two minutes in a 100 ppm solution of the compounds of this invention. Additional sections were dipped in a check solution which contained 500 ppm Alkanol ® XC (sodium alkyl naphthalene sulfonate). After inoculation by placing a mycelial plug of Sclerotinia sclerotiorum on each carrot section, the test was held at 20° C. for six days.

The untreated carrot sections were completely invaded with the mycelial growth of white mold fungus, but the treated sections had little or no growth by this disease causing organism.

TABLE 6

| Compounds | % control White Mold |
|---|---|
| N-[N-[2-chloro-5-(trifluoromethyl)phenyl]-N-[2,4-dinitro-6-(trifluoromethyl)phenyl]-aminothio]-N,4-dimethylbenzenesulfonamide | 100 |
| N-butyl-N-[N-[2-chloro-5-(trifluoromethyl)phenyl]-N-[2,4-dinitro-6-(trifluoromethyl)phenyl]aminothio]-2-methylbenzenesulfonamide | 100 |
| N-[N-[2-chloro-5-(trifluoromethyl)phenyl]-N-[2,4-dinitro-6-(trifluoromethyl)phenyl]-aminothio]-4-methyl-N-(1-methylethyl)-benzenesulfonamide | 100 |
| N-butyl-N-[N-[2-chloro-5-(trifluoromethyl)phenyl]-N-[2,4-dinitro-6-(trifluoromethyl)phenyl]aminothio]-4-methylbenzenesulfonamide | 86 |
| N-butyl-N-[N-[2-chloro-5-(trifluoromethyl)phenyl]-N-[2,4-dinitro-6-(trifluoromethyl)phenyl]aminothio]benzenesulfonamide | 86 |

The miticidal, insecticidal, ovicidal and fungicidal compositions of this invention may contain, in addition to a compound of this invention, other agricultural pesticides or adjuvants. The addition of compounds such as insecticides, miticides, bactericides, nematicides, fungicides or other agricultural chemicals, such as growth modifying agents, often increase the effectiveness of the composition and broaden its scope of control. Pesticides with which the compounds of this invention may be mixed to achieve broader-spectrum activity include:

Fungicides:
methyl 2-benzimidazolecarbamate (carbendazim)
tetramethyl thiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl).
N-trichloromethylthiotetrahydrophthalimide (captan)
N-trichloromethylthiophthalimide (folpet)
Bactericides:
tribasic copper sulfate
streptomycin sulfate
Acaricides:
senecioic acid, ester with 2-sec-butyl-4,6-dinitrophenol ("Morocide")
O,O-diethyl O-(3-chloro-4-methyl-2-oxo-2H-1-benzapyran-7-yl)phosphorothioate (Co-Ral ®)
O,O-dimethyl O-(2,4,5-trichlorophenyl)phosphorothioate (Ronnel ®)
6-methyl-1,3-dithiolo[2,3,-β]quinoxolin-2-one ("Morestan")
ethyl 4,4'-dichlorobenzilate (Chlorobenzilate ®)
1,1-bis(p-chlorophenyl)-2,2,2-trichloroethanol (Kelthane ®)
bis(pentachloro-2,4-cyclopentadien-1-yl) (Pentac ®)
tricyclohexyltin hydroxide (Plictran ®)
Nematicides:
S-methyl 1-(dimethylcarbamoyl)-N-(methylcarbamoyloxy)-thioformimidate (Vydate ®)
S-methyl 1-carbamoyl-N-(methylcarbamoyloxy)thioformimidate
N-isopropylphosphoramidic acid, 0-ethyl-0'-[4-(methylthio)-m-tolyl]diester ("Nemacur")
Insecticides:
3-hydroxy-N-methylcrotonamide(dimethylphosphate)ester (Azodrin ®)
methylcarbamic acid, ester with 2,3-dihydro-2,2-dimethyl-7-benzofuranol (Furadan ®)
0-[2,4,5-trichloro-α-(chloromethyl)benzyl]phosphoric acid, 0',0'-dimethyl ester (Gardona ®)
2-mercaptosuccinic acid, diethyl ester, S-ester with thionophosphoric acid, dimethyl ester (Malathion ®)
phosphorothioic acid, O,O-dimethyl,O-p-nitrophenyl ester (methyl parathion)
methylcarbamic acid, ester with α-naphthol (Sevin ®)
methyl O-(methylcarbamoyl)thiolacetohydroxamate (methomyl)
O,O-diethyl-O-(2-isopropyl-4-methyl-6-pyrimidyl)phosphorothioate (Diazinon ®)

octachlorocamphene (toxaphene)
O-ethyl O-p-nitrophenyl phenylphosphonothioate (EPN)
cyano(3-phenoxyphenyl)methyl 4-chloro-α-(1-methylethyl)benzeneacetate (Pydrin ®)
(3-phenoxyphenyl)methyl(+)-cis,trans-3-(2,2-dichloroethenyl)-2,2-dimethylcycloprpanecarboxylate (Ambush ®)
O-ethyl-S-(p-chlorophenyl)ethylphosphonodithioate (Curacron ®)
phosphorothiolothionic acid, O-ethyl-O-[4-(methylthio)-phenyl]-S-n-propyl ester (Bolstar ®)
2,2-bis(p-methoxyphenyl)-1,1,1-trichloroethane (methoxychlor)

The agricultural chemicals listed above are merely exemplary of compounds that may be mixed with the active compounds of this invention.

What is claimed is:

1. A compound of the formula:

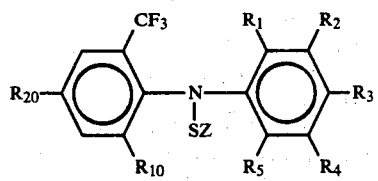

wherein
$R_1$, $R_3$ and $R_4$ are independently H, F, Cl, Br, $NO_2$, $CF_3$, $OCF_3$, $OCF_2CF_2H$ or $S(O)_kR_9$;
$R_2$ is H, F, Cl, Br, $NO_2$, $CF_3$ or $S(O)_kR_9$;
$R_5$ is H, Cl, F, Br or $NO_2$;
Z is $-NR_6SO_2R_{13}$,

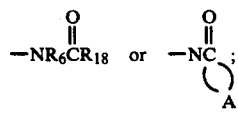

$R_6$ is $C_1-C_8$ alkyl, $C_3-C_5$ alkoxyalkyl, $C_2-C_4$ chloroalkyl,

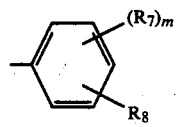

or $R_{14}CHCOR_{15}$;
$R_7$ is H, $C_1-C_{12}$ alkyl, $C_1-C_4$ alkoxy, Cl, Br or F;
$R_8$ is H, $C_1-C_4$ alkyl, $C_1-C_4$ alkoxy, Cl, Br, F, $CF_3$, $NO_2$, $R_{11}S(O)_k$ or $CO_2R_{12}$;
$R_9$ is $C_1-C_2$ alkyl or $C_1-C_2$ alkyl substituted with 2 to 4 atoms or Cl and/or F;
$R_{10}$ is H, $NO_2$ or $CF_3$;
$R_{11}$ is $C_1-C_2$ alkyl or $C_2-C_4$ dialkylamino,
$R_{12}$ is $C_1-C_4$ alkyl;
$R_{13}$ is

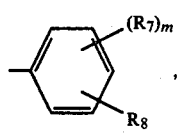

naphthyl, $NR_{16}R_{17}$, $CF_3$ or $C_1-C_{20}$ alkyl;

$R_{14}$ is H or $CH_3$;
$R_{15}$ is $C_1-C_4$ alkoxy or $N(R_{17})_2$;
$R_{16}$ is $C_1-C_3$ alkyl, $OCH_3$ or

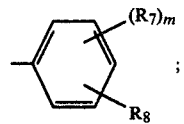

$R_{17}$ is $C_1-C_3$ alkyl;
$R_{18}$ is H, $C_1-C_8$ alkyl,

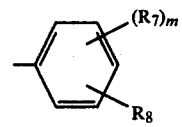

or $NR_{16}R_{17}$;
A is $-(CH_2)_3-$, $-(CH_2)_4-$, $-(CH_2)_5-$, $X(CH_2)_2-$ or $-X(CH_2)_3-$, where X is O, S, or $NR_{19}$ and where X is bonded to the carbonyl carbon of Z;
$R_{19}$ is $C_1-C_4$ alkyl, or phenyl optionally substituted with 1 or 2 groups selected from F, Cl, Br, $CH_3$ or $OCH_3$;
$R_{20}$ is $NO_2$ or $CF_3$;
k is 0, 1 or 2; and
m is 1 or 2;
provided that
(1) at least two of $R_1$, $R_2$, $R_3$, $R_4$ and $R_5$ are hydrogen;
(2) no more than two of the substituents $R_1$, $R_2$, $R_3$ and $R_4$ are simultaneously $NO_2$ or $CF_3$;
(3) when two $NO_2$ or two $S(O)_kR_9$ groups are present, they are not ortho to one another;
(4) only one of $R_6$ and $R_{13}$ or one of $R_6$ and $R_{16}$ or one of $R_6$ and $R_{18}$ is

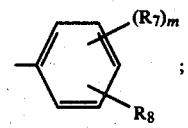

(5) when $R_{11}$ is dialkylamino, then k is 2; and
(6) $R_{10}$ and $R_{20}$ are not simultaneously $CF_3$;
and further provided that when $R_{10}$ is $NO_2$, then
(a) $R_1$ is H, F or Cl when $R_3$ is other than H, F or Cl;
(b) when $R_1=R_3=R_5$, then $R_1$, $R_3$ and $R_5$ are either H or F; and
(c) $R_5$ is either H or F.

2. A compound of claim 1 where $R_1$ is F, Cl, Br, $CF_3$, $OCF_3$, $OCF_2CF_2H$ or $S(O)_kCF_3$.

3. A compound of claim 1 where $R_2$ is H, F, Cl or Br.

4. A compound of claim 1 where $R_3$ is H, F, Cl, Br or $S(O)_kCF_3$.

5. A compound of claim 1 where $R_4$ is F, Cl, Br, $CF_3$, $OCF_3$, $OCF_2CF_2H$ or $S(O)_kCF_3$.

6. A compound of claim 1 where $R_6$ is $C_1-C_4$ alkyl.

7. A compound of claim 1 where $R_7$ is H, $C_1-C_3$ alkyl, $C_1-C_3$ alkoxy or Cl.

8. A compound of claim 1 where $R_8$ is H, $C_1-C_3$ alkyl or Cl.

9. A compound of claim 1 where $R_{10}$ is $NO_2$.

10. A compound of claim 1 where $R_{13}$ is

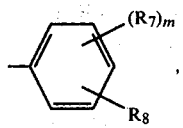

naphthyl, $NR_{16}R_{17}$ or $C_1-C_3$ alkyl, where $R_{16}$ and $R_{17}$ are independently $C_1-C_2$ alkyl.

11. A compound of claim 1 where
$R_1$ and $R_4$ are independently Cl, $CF_3$, $OCF_3$, $S(O)_kCF_3$;
$R_2$ and $R_5$ are H;
$R_3$ is H or $S(O)_kCF_3$;
$R_6$ is $C_1-C_4$ alkyl;
$R_7$ is H, $C_1-C_3$ alkyl, $C_1-C_3$ alkoxy or Cl;
$R_8$ is H, $C_1-C_3$ alkyl or Cl;
$R_{10}$ is $NO_2$; and
$R_{13}$ is

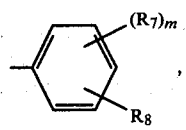

2-naphthyl, $N(CH_3)_2$ or $CH_3$.

12. A compound of claim 1, N-[N-[2-chloro-5-(trifluoromethyl)phenyl]-N-[2,4-dinitro-6-(trifluoromethyl)phenyl]aminothio]-N,4-dimethylbenzenesulfonamide.

13. A compound of claim 1, N-butyl-N-[N-[2-chloro-5-(trifluoromethyl)phenyl]-N-[2,4-dinitro-6-(trifluoromethyl)phenyl]aminothio]-2-methylbenzenesulfonamide.

14. A compound of claim 1, N-[N-[2-chloro-5-(trifluoromethyl)phenyl]-N-[2,4-dinitro-6-(trifluoromethyl)phenyl]aminothio]-4-methyl-N-(1-methylethyl)-benzenesulfonamide.

15. A compound of claim 1, N-butyl-N-[N-[2-chloro-5-(trifluoromethyl)phenyl]-N-[2,4-dinitro-6-(trifluoromethyl)phenyl]aminothio]-4-methylbenzenesulfonamide.

16. A compound of claim 1, N-butyl-N-[N-[2-chloro-5-(trifluoromethyl)phenyl]-N-[2,4-dinitro-6-(trifluoromethyl)phenyl]aminothio]-benzenesulfonamide.

17. A compound of claim 1, N-[N-[2-chloro-5-(trifluoromethyl)phenyl]-N-[2,4-dinitro-6-(trifluoromethyl)phenyl]aminothio]-N-(4-methylphenylsulfonyl)glycine methyl ester.

18. A compound of claim 1, N-[N-[2,4-dinitro-6-(trifluoromethyl)phenyl]-N-(2,4,6-trifluorophenyl)aminothio]-N,4-dimethylbenzenesulfonamide.

19. A compound of claim 1, N-[2-chloro-5-(trifluoromethyl)phenyl]-N-[2,4-dinitro-6-(trifluoromethyl)phenyl]-2-oxo-1-pyrrolidinesulfenamide.

20. A compound of claim 1, N-[N-[2-chloro-5-(trifluoromethyl)phenyl]-N-[2,4-dinitro-6-(trifluoromethyl)phenyl]aminothio]-N-methyl-2-naphthalenesulfonamide.

21. A compound of claim 1, N-[N-[2-chloro-5-(trifluoromethyl)phenyl]-N-[2,4-dinitro-6-(trifluoromethyl)phenyl]aminothio]-N-butyl-N',N'-dimethylsulfamide.

22. A compound of claim 1, N-butyl-N-[N-[2-chloro-5-(trifluoromethyl)phenyl]-N-[2,4-dinitro-6-(trifluoromethyl)phenyl]aminothio]-methanesulfonamide.

23. A compound of claim 1, N-[N-[2-chloro-5-(trifluoromethyl)phenyl]-N-[2,4-dinitro-6-(trifluoromethyl)phenyl]aminothio]-N-(1,1-dimethylethyl)-4-methylbenzenesulfonamide.

24. A compound of claim 1, N-[N-[2-chloro-5-trifluoromethylphenyl]-N-[2,4-dinitro-6-trifluoromethylphenyl]aminothio]-N-(2-methoxyethyl)-4-methylbenzenesulfonamide.

25. A composition suitable for control of mites comprising a miticidally effective amount of a compound of claim 1 and at least one of (a) a diluent and (b) a surfactant.

26. A composition suitable for control of insects or insect eggs comprising an insecticidally or ovicidally effective amount of a compound of claim 1 and at least one of (a) a diluent and (b) a surfactant.

27. A composition suitable for control of fungus disease of a plant comprising a fungicidally effective amount of a compound of claim 1 and at least one of (a) a diluent and (b) a surfactant.

28. A method for control of mites which comprises applying to a locus of infestation, to the area to be protected or to the pests themselves a miticidally effective amount of a compound of claim 1.

29. A method for control of insects or insect eggs which comprises applying to a locus of infestation, to the area to be protected or to the pests or eggs themselves, an insecticidally or ovicidally effective amount of a compound of claim 1.

30. A method for controlling fungus disease of a plant which comprises applying to the seed from which the plant is to be grown, to the portion of the plant to be protected or to the media in which the plant is growing a fungicidally effective amount of a compound of claim 1.

31. A process for preparing a compound of the formula:

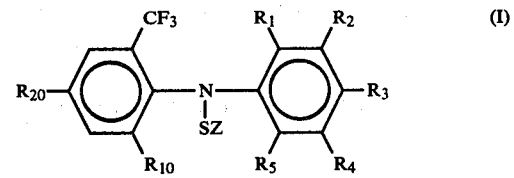

wherein
$R_1$, $R_3$ and $R_4$ are independently H, F, Cl, Br, $NO_2$, $CF_3$, $OCF_3$, $OCF_2CF_2H$ or $S(O)_kR_9$;
$R_2$ is H, F, Cl, Br, $NO_2$, $CF_3$ or $S(O)_kR_9$;
$R_5$ is H, Cl, F, Br, or $NO_2$;
Z is $-NR_6SO_2R_{13}$,

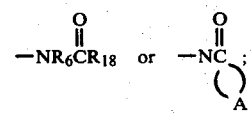

$R_6$ is $C_1-C_8$ alkyl, $C_3-C_5$ alkoxyalkyl, $C_2-C_4$ chloroalkyl,

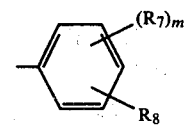

or $R_{14}CHCOR_{15}$;

$R_7$ is H, $C_1$-$C_{12}$ alkyl, $C_1$-$C_4$ alkoxy, Cl, Br or F;

$R_8$ is H, $C_1$-$C_4$ alkyl, $C_1$-$C_4$ alkoxy, Cl, Br, F, $CF_3$, $NO_2$, $R_{11}S(O)_k$ or $CO_2R_{12}$;

$R_9$ is $C_1$-$C_2$ alkyl or $C_1$-$C_2$ alkyl substituted with 2 to 4 atoms or Cl and/or F;

$R_{10}$ is H, $NO_2$ or $CF_3$;

$R_{11}$ is $C_1$-$C_2$ alkyl or $C_2$-$C_4$ dialkylamino, $R_{12}$ is $C_1$-$C_4$ alkyl;

$R_{13}$ is

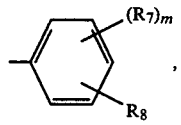, naphthyl, $NR_{16}R_{17}$, $CF_3$ or $C_1$-$C_{20}$ alkyl;

$R_{14}$ is H or $CH_3$;

$R_{15}$ is $C_1$-$C_4$ alkoxy or $N(R_{17})_2$;

$R_{16}$ is $C_1$-$C_3$ alkyl, $OCH_3$ or

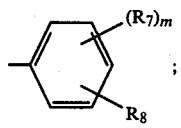;

$R_{17}$ is $C_1$-$C_3$ alkyl;

$R_{18}$ is H, $C_1$-$C_8$ alkyl,

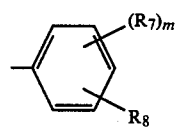

or $NR_{16}R_{17}$;

A is $-(CH_2)_3-$, $-(CH_2)_4-$, $-(CH_2)_5-$, $X(CH_2)_2-$ or $-X(CH_2)_3-$, where X is O, S or $NR_{19}$ and where X is bonded to the carbonyl carbon of Z;

$R_{19}$ is $C_1$-$C_4$ alkyl, or phenyl optionally substituted with 1 or 2 groups selected from F, Cl, Br, $CH_3$ or $OCH_3$;

$R_{20}$ is $NO_2$ or $CF_3$;

k is 0, 1 or 2; and m is 1 or 2;

provided that (1) at least two of $R_1$, $R_2$, $R_3$, $R_4$ and $R_5$ are hydrogen;

(2) no more than two of the substituents $R_1$, $R_2$, $R_3$ and $R_4$ are simultaneously $NO_2$ or $CF_3$;

(3) when two $NO_2$ or two $S(O)_kR_9$ groups are present, they are not ortho to one another;

(4) only one of $R_6$ and $R_{13}$ or one of $R_6$ and $R_{16}$ or one of $R_6$ and $R_{18}$ is

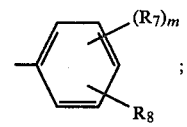;

(5) when $R_{11}$ is dialkylamino, then k is 2; and (6) $R_{10}$ and $R_{20}$ are not simultaneously $CF_3$; and further provided that when $R_{10}$ is $NO_2$, then (a) $R_1$ is H, F or Cl when $R_3$ is other than H, F or Cl;

(b) when $R_1=R_3=R_5$, then $R_1$, $R_3$ and $R_5$ are either H or F; and (c) $R_5$ is either H or F; consisting essentially of (a.) contacting a compound of the formula

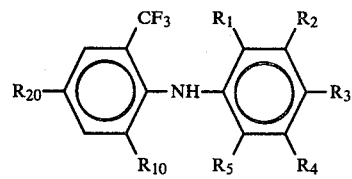

where $R_1$, $R_2$, $R_3$, $R_4$, $R_5$, $R_{10}$ and $R_{20}$ are as defined above, with an equivalent amount of a metal hydride or alkali hydroxide; and (b.) contacting the product of (a) with an equivalent or excess of a sulfenyl chloride of the formula ClSZ, where Z is as defined above.

* * * * *